US009421193B2

(12) United States Patent
Hong et al.

(10) Patent No.: US 9,421,193 B2
(45) Date of Patent: Aug. 23, 2016

(54) BENZOTHIAZOLE DERIVATIVES AND A USE THEREOF FOR THE TREATMENT OF CANCER

(71) Applicant: Korea Institute of Radiological & Medical Sciences, Seoul (KR)

(72) Inventors: Sung Hee Hong, Seoul (KR); In Seok Hong, Yongin-si (KR); Kee Ho Lee, Seoul (KR)

(73) Assignee: Korea Institute of Radiological & Medical Sciences, Seoul (KR)

( * ) Notice: Subject to any disclaimer, the term of this patent is extended or adjusted under 35 U.S.C. 154(b) by 0 days.

(21) Appl. No.: 14/992,895

(22) Filed: Jan. 11, 2016

(65) Prior Publication Data

US 2016/0120851 A1    May 5, 2016

Related U.S. Application Data

(63) Continuation of application No. 14/335,733, filed on Jul. 18, 2014, now Pat. No. 9,266,875.

(51) Int. Cl.
C07D 417/12 (2006.01)
A61K 31/428 (2006.01)

(52) U.S. Cl.
CPC ............ *A61K 31/428* (2013.01); *C07D 417/12* (2013.01)

(58) Field of Classification Search
CPC .......................... C07D 417/12; A61K 31/428
See application file for complete search history.

(56) References Cited

U.S. PATENT DOCUMENTS 9,266,875 B2 * 2/2016 Hong .................. C07D 417/12

FOREIGN PATENT DOCUMENTS

KR     20130128693 A  * 11/2013
WO    WO 2009/149054 A1   12/2009

OTHER PUBLICATIONS

Elrod et al. PPAR Research, 2008, pp. 1-12.*
Luo et al. Cell, 2009, 136, pp. 823-837.*
CAS Registry Entry for Registry No. 1022492-98-3, which entered STN on May 25, 2008.
CAS Registry Entry for Registry No. 1022842-27-8, which entered STN on May 27, 2008.
Chang et al. "Induction of differentiation and apoptosis by ligands of peroxisome proliferator-activated receptor gamma in non-small cell lung cancer," *Cancer Res.*, Feb. 15, 2000;60(4):1129-38.
Elstner, et al. "Ligands for peroxisome proliferator-activated receptorgamma and retinoic acid receptor inhibit growth and induce apoptosis of human breast cancer cells in vitro and in BNX mice," *Proc Natl Acad Sci U S A.*, Jul. 21, 1998;95(15):8806-11.
Fukumoto et al. "Peroxisome proliferator-activated receptor delta as a molecular target to regulate lung cancer cell growth, "*FEBS Lett.*, Jul. 4, 2005;579(17):3829-36.
Girnun et al. "Regression of drug-resistant lung cancer by the combination of rosiglitazone and carboplatin," Clin Cancer Res., Oct. 15, 2008;14(20):6478-86.
Govindarajan et al. "Thiazolidinediones and the risk of lung, prostate, and colon cancer in patients with diabetes," *J Clin Oncol.*, Apr. 20, 2007;25(12):1476-81.
Han et al., "Anticancer actions of PPARγ ligands: Current state and future perspectives in human lung cancer," *World J Biol Chem*, Mar. 26, 2010; 1(3): 31-40.
Müller-Brüsselbach et al. "Growth of transgenic RAF-induced lung adenomas is increased in mice with a disrupted PPARbeta/delta gene," *Int J Oncol.*, Sep. 2007;31(3):607-11.
Sarraf et al., "Differentiation and reversal of malignant changes in colon cancer through PPARgamma," *Nat Med.* Sep. 1998;4(9):1046-52.
Tsubouchi et al. "Inhibition of human lung cancer cell growth by the peroxisome proliferator-activated receptor-gamma agonists through induction of apoptosis," *Biochem Biophys Res Commun.*, Apr. 13, 2000;270(2):400-5.
Wang et al. "Induction of apoptosis by 15d-PGJ2 via ROS formation: An alternative pathway without PPARγ activation in non-small cell lung carcinoma A549 cells," *Prostagladins & other Lipid Mediators*, 2011;94;104-111.
Zhang et al. "Influence of ciglitazone on A549 cells growth in vitro and in vivo and mechanism," *J Huazhong Univ Sci Technol Med Sci.*, 2006;26(1):36-39.

* cited by examiner

*Primary Examiner* — Matthew Coughlin
(74) *Attorney, Agent, or Firm* — Klarquist Sparkman, LLP

(57) ABSTRACT

Provided are a compound represented by Formula I, a pharmaceutically acceptable salt thereof, or a solvate thereof; and a pharmaceutical composition for cancer treatment and a pharmaceutical composition for a radiation sensitizer for cancer treatment, each pharmaceutical composition including the compound of Formula I, the pharmaceutically acceptable salt thereof, or the solvate thereof:

[Formula I]

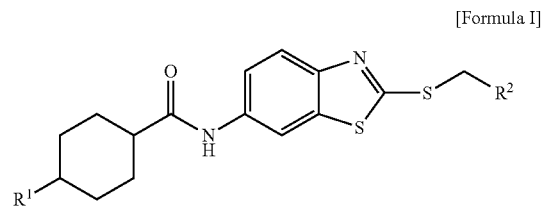

wherein, in Formula I,
—$R^1$ is a $C_1$-$C_3$ alkoxy, =O, or —OH, and
—$R^2$ is a 5- or 6-membered heteroaryl including 1 to 2 hetero atoms selected from nitrogen and oxygen, wherein a carbon of the 5- or 6-membered heteroaryl is optionally substituted with a $C_1$-$C_3$ alkyl a $C_1$-$C_3$ alkoxy, or hydroxy.

5 Claims, 20 Drawing Sheets

FIG. 12

| TREATMENT GROUP | | EXPECTED SURVIVAL RATIO | ACTUAL SURVIVAL RATIO | EXPECTED SURVIVAL RATIO / ACTUAL SURVIVAL RATIO | DOSE INCREASE RATE |
|---|---|---|---|---|---|
| 2 Gy + | Cig 10uM | 0.022875 | 0.112 | 0.2042411 | 1.3616071 |
| | PB01 10uM | 0.021675 | 0.009 | 0.2408333 | 1.6666667 |
| | PB11 5uM | 0.022725 | 0.0935 | 0.0935 | 1.5882353 |
| | PB11 10uM | 0.0204 | 0.0165 | 0.0165 | 9.0909091 |
| 4 Gy + | Cig 10uM | 0.0129625 | 0.067 | 0.1934701 | 0.2686567 |
| | PB01 10uM | 0.0122825 | 0.0475 | 0.2585789 | 1.7894737 |
| | PB11 5uM | 0.0128775 | 0.044 | 0.2926705 | 1.9318182 |
| | PB11 10uM | 0.01156 | 0.0115 | 1.0052174 | 7.3913043 |

BENZOTHIAZOLE DERIVATIVES AND A USE THEREOF FOR THE TREATMENT OF CANCER

CROSS REFERENCE TO RELATED APPLICATION

This is a continuation of U.S. patent application Ser. No. 14/335,733, filed Jul. 18, 2014, which is incorporated herein by reference in its entirety.

BACKGROUND

1. Field

One or more embodiments of the present invention relate to novel benzothiazole derivative compounds effective for cancer treatment, and more particularly, to a benzothiazole derivative compound, a use of the benzothiazole derivative compound for cancer treatment, and a use of the benzothiazole derivative compound as a radiation sensitizer for cancer treatment.

2. Description of the Related Art

Even with the recent sharp increase in cancer incidence due to rapid industrial development, global ecosystem changes, and dietary changes, cancer is still an incurable disease due to the yet unidentified incidence mechanism of cancer. Anticancer drugs in current use may be largely classified into biological drugs, such as enzymatic drugs or vaccines, pure synthetic drugs, and drugs derived from natural products. Anticancer drugs may exhibit various pharmacological actions depending on the types of cancer and have various side effects due to toxicity, and thus, may be problematic in cancer treatment. Anticancer drugs may effectively suppress the growth of cancer cells, but also have toxicity to normal cells. Due to this, many scholars have done research to develop a more effective anticancer drug having minimum toxicity to normal cells.

Lung cancer is the second most prevalent cancer, next to gastric cancer, and has been first in mortality among other cancers since the year 2000, due to a poor prognosis. Lung cancer may be histologically classified into small-cell lung cancer or non-small cell lung cancer. Chemotherapy and radiotherapy are recommended for small-cell lung cancer, and radical lumpectomy is known as the best treatment for non-small cell lung cancer. Lung cancer may have a difficulty in local tumor control, and may include micro-metastatic cancer cell that are likely undetectable by diagnostic imaging. Accordingly, local radiotherapy alone on a lung may lead to metastasis to other remote organs, with a 5-year survival rate of less than 10%. Accordingly, a various combinations of radiotherapy with chemotherapy have been used to prevent the recurrence of cancer in remote organs and have been found to be more effective than radiotherapy only.

Peroxisome proliferator activated receptors (PPARs) which are nuclear receptors belonging to the steroid-thyroid-retinoid receptor superfamily are transcription factors of which activities are regulated by various ligands. PPARs are also key factors to regulate sugar and lipid metabolisms, and are also known to regulate cell division, cell differentiation, and cell death in various tissues. Activation of PPAR is known to exhibit anticancer activity in various cancers.

Thiazolidinediones as a diabetes treatment drug, including troglitazone (TGZ), ciglitazone, rosiglitazone, or pioglitazone, are synthetic PPARγ agonists. Reportedly, TGZ is known to have a cytotoxic effect on various human cancers of the colon (Non-patent document 1), the breast (Non-patent document 2), the liver, the lungs, the kidneys, and the prostate.

It has been suggested that the activation of PPAR β/δ ameliorates lung cancer. High-affinity synthetic ligand for PPAR β/δ, such as L165041, was found to suppress cell proliferation in human lung cancer (Non-patent document 3) and to exacerbate lung cancer in a transgenic mouse lacking the gene expression of PPAR β/δ (Non-patent document 4).

The expression of PPAR γ prognosis was found to be reduced in lung cancer patients with a poor prognosis (Non-patent document 8). The activation of PPAR γ by an endogenous agonist or a synthetic agonist was found to suppress the growth of lung cancer (Non-patent document 5). The treatment of non-small cell lung cancer with PPAR γ active materials was reported to induce apoptosis and differentiation (Non-patent document 6). Ciglitazone was reported to suppress tumors derived from A-549 cells in nude mice (Non-patent document 7). Diabetes patients administered with thiazolidinedione known as PPAR γ agonist to treat diabetes were found to have a remarkably low likelihood of developing lung cancer (Non-patent document 8). The reaction of PPAR-γ ligands was found to protect the body from lung cancer (Non-patent documents 9 and 10).

PPAR-γ ligands are known to have anticancer functions through dependent or independent pathways on PPAR-γ, and in particular, the latter was found to be related with lung cancer (Non-patent document 11).

PRIOR ART DOCUMENTS

List of Non-Patent Documents

1. Sarraf P, Mueller E, Jones D, King F J, DeAngelo D J, Partridge J B, Holden S A et al., Differentiation and reversal of malignant changes in colon cancer through PPAR-gamma. Nat Med. 1998 September; 4(9):1046-52.
2. Elstner E, Müller C, Koshizuka K, Williamson E A, et al., Ligands for peroxisome proliferator-activated receptor-gamma and retinoic acid receptor inhibit growth and induce apoptosis of human breast cancer cells in vitro and in BNX mice. Proc Natl Acad Sci USA. 1998 Jul. 21; 95(15):8806-11.
3. Fukumoto K, Yano Y, Virgona N, Hagiwara H, et al., Peroxisome proliferator-activated receptor delta as a molecular target to regulate lung cancer cell growth. FEBS Lett. 2005 Jul. 4; 579(17):3829-36.
4. Müller-Brüsselbach S, Ebrahimsade S, Jakel J, Eckhardt J, Rapp U R, Peters J M, et al., Growth of transgenic RAF-induced lung adenomas is increased in mice with a disrupted PPARbeta/delta gene. Int J Oncol. 2007 September; 31(3):607-11.
5. Tsubouchi Y, Sano H, Kawahito Y, Mukai S, Yamada R, Kohno M, Inoue K, et al., Inhibition of human lung cancer cell growth by the peroxisome proliferator-activated receptor-gamma agonists through induction of apoptosis. Biochem Biophys Res Commun. 2000 Apr. 13; 270(2):400-5.
6. Chang T H, Szabo E. Induction of differentiation and apoptosis by ligands of peroxisome proliferator-activated receptor gamma in non-small cell lung cancer. Cancer Res. 2000 Feb. 15; 60(4):1129-38.
7. Zhang W, Zhang H, Xing L., Influence of ciglitazone on A549 cells growth in vitro and in vivo and mechanism. J Huazhong Univ Sci Technol Med Sci. 2006; 26(1):36-39.
8. Govindarajan R, Ratnasinghe L, Simmons D L, Siegel E R, Midathada M V, Kim L, Kim P J, et al., Thiazolidinediones and the risk of lung, prostate, and colon cancer in patients with diabetes. J Clin Oncol. 2007 Apr. 20; 25(12):1476-81.
9. Girnun G D, Chen L, Silvaggi J, Drapkin R, Chirieac L R, Padera R F, Upadhyay R, et al., Regression of drug-resistant lung cancer by the combination of rosiglitazone and carboplatin. Clin Cancer Res. 2008 Oct. 15; 14(20):6478-86.
10. Shou Wei Han et al., Anticancer actions of PPARγ ligands: Current state and future perspectives in human lung cancer, World J Biol Chem 2010 Mar. 26; 1(3): 31-40.
11. Jun-Jie Wang, Oi-Tong Mak. Induction of apoptosis by 15d-PGJ2 via ROS formation: An alternative pathway without PPARγ activation in non-small cell lung carcinoma A549 cells. Prostaglandins & other Lipid Mediators 2011; 94; 104-111.

SUMMARY

One or more embodiments of the present invention include novel compounds able to function as PPAR-γ ligands and radiation sensitizers and anticancer agents.

One or more embodiments of the present invention include pharmaceutical compositions for cancer treatment that include the novel compounds.

One or more embodiments of the present invention include pharmaceutical compositions for a radiation sensitizer for cancer treatment that include the novel compounds.

Additional aspects will be set forth in part in the description which follows and, in part, will be apparent from the description, or may be learned by practice of the presented embodiments.

According to one or more embodiments of the present invention, there is provided a compound of Formula I, a pharmaceutically acceptable salt thereof, or a solvate thereof:

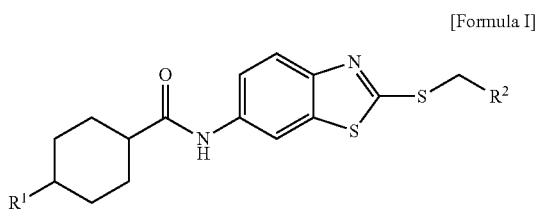

[Formula I]

wherein, in Formula I,
—$R^1$ is a $C_1$-$C_3$ alkoxy, =O or —OH, and
—$R^2$ is a 5- or 6-membered heteroaryl including 1 to 2 hetero atoms selected from nitrogen and oxygen, wherein a carbon of the 5- or 6-membered heteroaryl is optionally substituted with a $C_1$-$C_3$ alkyl, a $C_1$-$C_3$ alkoxy, or hydroxy.

According to one or more embodiments of the present invention, a pharmaceutical composition for cancer treatment includes a compound of Formula 1, a pharmaceutically acceptable salt thereof, or a solvate thereof according to the above-description.

According to one or more embodiments of the present invention, a pharmaceutical composition for a radiation sensitizer for cancer treatment includes a compound of Formula 1, a pharmaceutically acceptable salt thereof, or a solvate thereof according to the above-description.

BRIEF DESCRIPTION OF THE DRAWINGS

These and/or other aspects will become apparent and more readily appreciated from the following description of the embodiments, taken in conjunction with the accompanying drawings in which:

FIG. 12 illustrates data obtained based on the results of colony counting of the non-small cell lung cancer cell strain H460 on a plate after treatment with ciglitazone (10 μM), PB01 (10 μM), or PB11 (5 μM, 10 μM), irradiation with γ-rays, and then incubation for 14 days.

DETAILED DESCRIPTION

Figure 1:
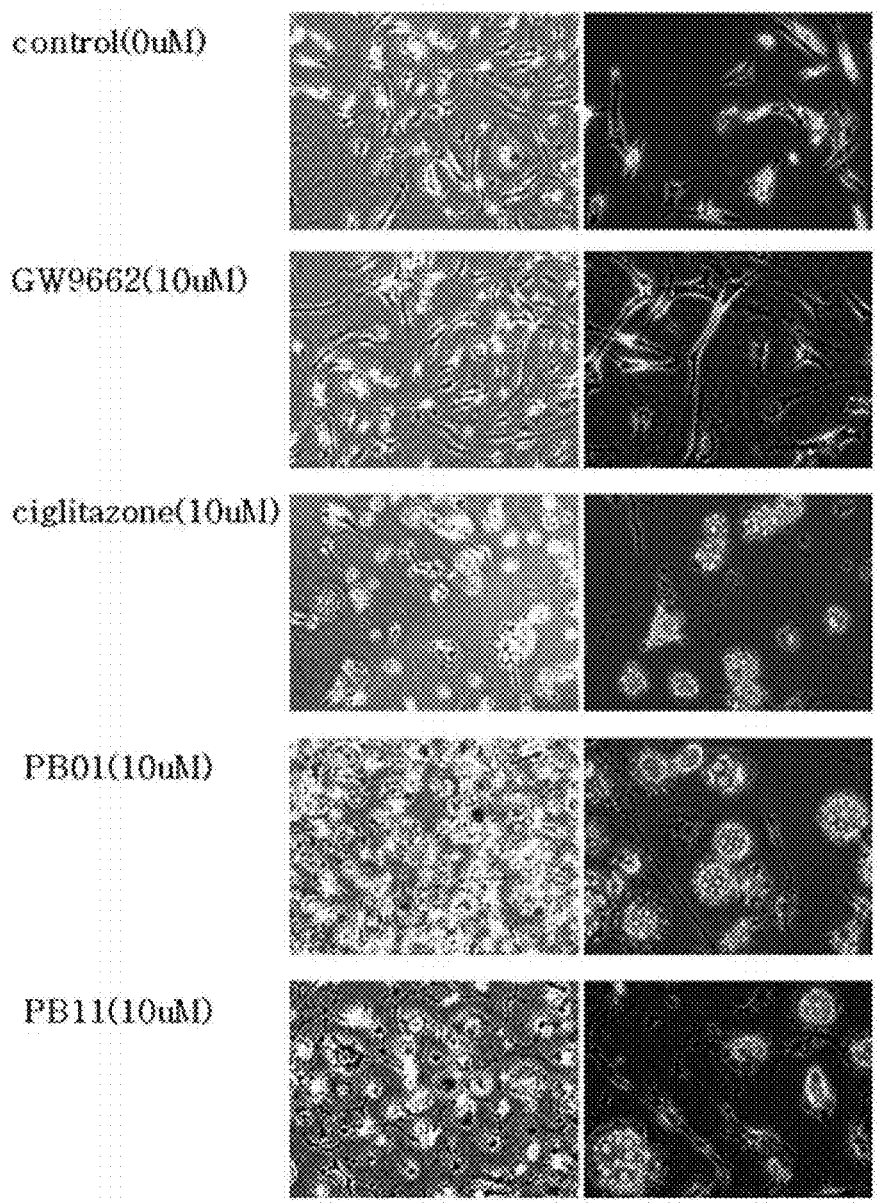
FIG. 1 illustrates the results of imaging degrees of adipogenesis via Oil-Red-O staining after treatment of 3T3-L1 cells with control compounds and 10 μM of compounds PB01 or PB11 of Examples 3 and 5 for about 48 hours (2 days) to induce adipogenesis.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Unless otherwise defined, all terms, including technical and scientific terms, used herein have the same meaning as commonly understood by one of ordinary skill in the art to which this invention belongs. It will also be appreciated that, although exemplary methods or compounds are described herein, all similarities or equivalents to the exemplary embodiments herein that do not depart from the spirit and scope of the present disclosure are encompassed in the present invention. The disclosures of reference documents, including non-patent documents, referred to herein are incorporated herein in their entirety by reference.

As a result of research into the development of novel compounds functioning as PPAR-γ ligands with anticancer activity, the present inventors developed novel benzothiazole derivative compounds.

According to an aspect of the present disclosure, there are provided a compound represented by Formula 1, a pharmaceutically acceptable salt thereof, or a solvate thereof:

In Formula I,

—$R^1$ may be a $C_1$-$C_3$ alkoxy, =O or —OH, and

—$R^2$ may be a 5- or 6-membered heteroaryl including 1 to 2 hetero atoms selected from nitrogen and oxygen, wherein a carbon of the 5- or 6-membered heteroaryl is optionally substituted with a $C_1$-$C_3$ alkyl, a $C_1$-$C_3$ alkoxy, or hydroxy.

For example, the compound of Formula I may be selected from the group consisting of 4-methoxy-cyclohexanecarboxylic acid [2-(3,5-dimethyl-isooxazole-4-yl)sulfanyl-benzothiazole-6-yl]-amide, 4-oxo-cyclohexanecarboxylic acid [2-(3,5-dimethyl-isoxazole-4-yl)sulfanyl-benzothiazole-6-yl]-amide, and 4-hydroxy-cyclohexanecarboxylic acid [2-(3, 5-dimethyl-isoxazole-4-yl)sulfanyl-benzothiazole-6-yl]-amide.

The pharmaceutically acceptable salt may be present as an acid addition salt with free acid. The compound of Formula I may form a pharmaceutically acceptable acid addition salt according to a common method known in the art. The free acid may be organic acid or inorganic acid. For example, the inorganic salt may be hydrochloric acid, bromic acid, sulfuric acid, or phosphoric acid. For example, the organic acid may be citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, galacturonic acid, embonic acid, glutamic acid, or aspartic acid The pharmaceutically acceptable salt may be present as an inorganic salt of the compound of Formula I. The compound of Formula I may form a pharmaceutically acceptable inorganic salt according to a common method known in the art. The inorganic salt may be a salt of aluminum, ammonium, calcium, copper, iron, lithium, magnesium, manganese, potassium, sodium, or zinc, but is not limited thereto. For example, the inorganic salt may be a salt of ammonium, calcium, magnesium, potassium, or sodium.

The compound of Formula I may be in the form of any salt, hydrate, or solvate that may be prepared using a common method in the art, in addition to such a pharmaceutically acceptable salt as described above.

The compound of Formula I may be synthesized by a method as represented in Reaction Scheme I.

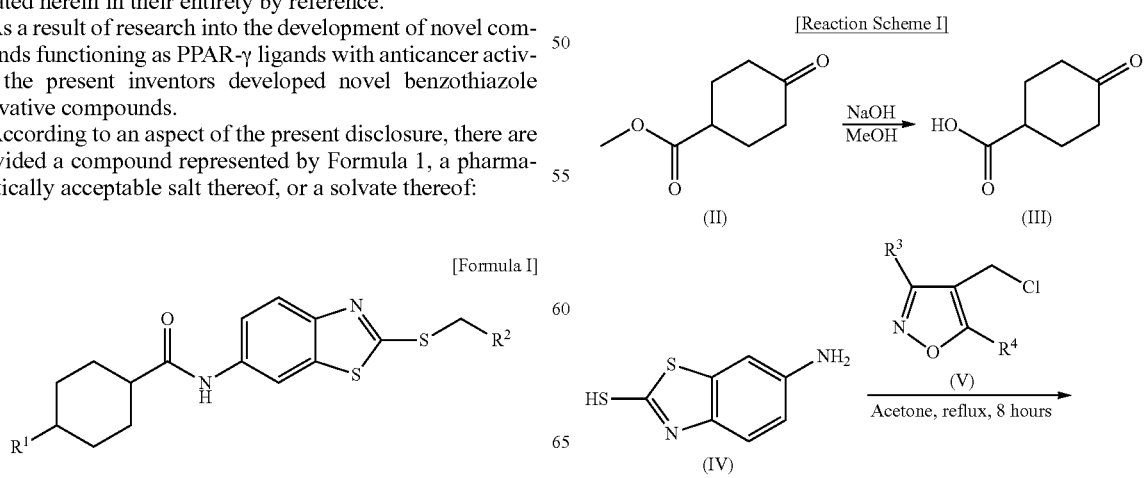

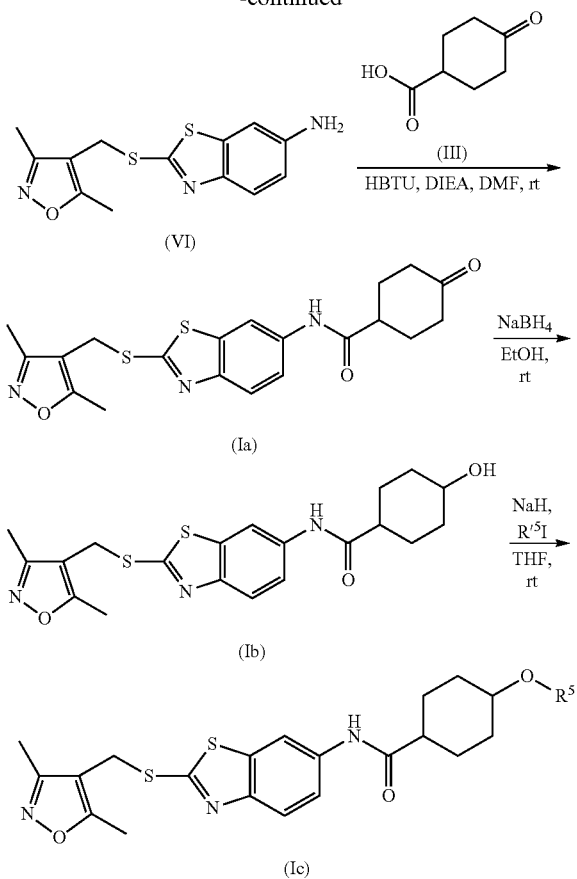

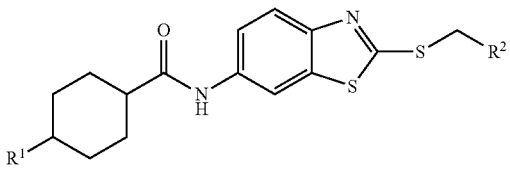

In Reaction Scheme I, $R^3$ and $R^4$ in Formula V may be each independently hydrogen, a $C_1$-$C_3$ alkyl, a $C_1$-$C_3$ alkoxy, or hydroxy. In Reaction Scheme I, $R^5$ may be a $C_1$-$C_3$ alkyl.

The synthesis method illustrated in Reaction Scheme I is described in more detail in Examples 1 to 5 described later. Although Examples 1 to 5 are described with specific functional groups for $R^3$, $R^4$, and $R^5$ of Formula V, it may be obvious to one of ordinary skill in the art of organic chemistry to change functional groups for $R^3$, $R^4$, and $R^5$ based on Reaction Scheme I and the synthesis method described in the examples. Although some embodiments of preparing the compound of Formula I are described herein, it may be obvious to one of ordinary skill in the art of organic chemistry to prepare the compound of Formula I differently than described herein by appropriately changing starting materials, reaction pathways, and reaction conditions.

The compound of Formula I was identified to be a PPAR γ ligand by Oil-Red-O staining (Example 6), and was found to suppress the growth of various cancer cells, including human colorectal cancer cells, breast cancer cells, non-small cell lung cancer cells, and leukemia cells, and in particular, to be more sensitive to suppress the growth of a non-small cell lung cancer cell strain, selectively only to cancer cells, without growth suppression or killing of non-cancer lung cells (Example 7). When treated with the compound of Formula I, cancer cells lost adhesion, with an increase in apoptotic body by chromatic agglutination and an increase in extracellular lactate dehydrogenase (LDH), indicating that the death of cancer cells is from apoptosis (Example 8). When used along with radiotherapy, the compound of Formula I was shown to have a dose increase rate of 1 or greater or 2 or less (Example 10), indicating that the compound of Formula I may be effective as a radiation sensitizer for cancer treatment.

According to another aspect of the present disclosure, there are provided a pharmaceutical composition for cancer treatment that includes a compound of Formula 1 below, a pharmaceutically acceptable salt thereof, or a solvate thereof:

[Formula I]

In Formula I,
—$R^1$ may be a $C_1$-$C_3$ alkoxy, =O or —OH, and
—$R^2$ may be a 5- or 6-membered heteroaryl including 1 to 2 hetero atoms selected from nitrogen and oxygen, wherein a carbon of the 5- or 6-membered heteroaryl is optionally substituted with a $C_1$-$C_3$ alkyl, a $C_1$-$C_3$ alkoxy, or hydroxy According to another aspect of the present disclosure, there is provided a pharmaceutical composition for a radiation sensitizer for cancer treatment, the pharmaceutical composition including a compound of Formula 1, a pharmaceutically acceptable salt thereof, or a solvate thereof as described above.

For example, the cancer may be bladder cancer, gastric cancer, colorectal cancer, esophageal cancer, pancreatic cancer, lung cancer, non-small cell lung cancer, colon cancer, bone cancer, skin cancer, skin or ocular melanoma, uterine cancer, rectal cancer, anal cancer, breast cancer, ovarian cancer, liver cancer, bronchial cancer, nasopharyngeal cancer, laryngeal cancer, brain cancer, leukocytes cancer, prostate cancer, kidney or ureter cancer, renal cell carcinoma, renal pelvic carcinoma, central nervous system (CNS) tumors, primary CNS lymphoma, spinal cord tumors, brainstem gliomas, or pituitary adenomas, but is not limited thereto. In some embodiments, the cancer may be lung cancer, breast cancer, colorectal cancer, or leukemia, and in some other embodiments, non-small cell lung cancer.

The pharmaceutical composition may be prepared in any common pharmaceutical dosage form known in the art. For example, the pharmaceutical dosage form may include any form of oral preparations, injections, suppositories, preparations for percutaneous administration or nasal administration, but is not limited thereto. For example, the pharmaceutical composition may be prepared as oral preparations or injections.

In formulating the pharmaceutical composition in any of the above-listed dosage forms, a pharmaceutically acceptable carrier appropriate for each dosage form may be further added. As used herein, the term "pharmaceutically acceptable carrier" refers to any additive ingredients excluding the pharmaceutically active ingredient. The term "pharmaceutically acceptable" refers to the properties that do not cause any pharmaceutically undesirable change via interaction between ingredients of the oral pharmaceutical compositions (for example, via interaction between carriers or via interaction between the pharmaceutically active ingredient and a carrier). Selection of the pharmaceutically acceptable carrier may be dependent on the properties and the administration method of a particular dosage form, the effects of the carrier on solubility and stability of the dosage form, and the like.

In some embodiments, the pharmaceutically acceptable carrier contained in the pharmaceutical composition for oral administration may be at least one selected from the group consisting of a diluent, a binder, a glidant (or a lubricant), a disintegrant, a stabilizer, a solubilizing agent, a sweetening agent, a coloring agent, and a flavoring agent.

The diluent refers to any excipient added to increase the volume of the oral pharmaceutical composition to formulate it into a target dosage form with an appropriate size. Non-limiting examples of the diluent may be starch (for example, potato starch, corn starch, wheat starch, pregelatinized starch), microcrystalline cellulose (for example, low-hydration microcrystalline cellulose), lactose (for example, lactose monohydrate, anhydrous lactose, spray lactose), glucose, sorbitol, mannitol, sucrose, alginate, alkaline earth metal salts, clay, polyethylene glycol, dicalcium phosphate, anhydrous calcium hydrogenphosphate, or silicon dioxide, which may be used alone or as a mixture thereof. In some embodiments, the excipient may be used from about 5 wt % to about 50 wt % based on a total weight of the pharmaceutical composition for oral administration. In some other embodiments, the excipient may be used from about 10 wt % to about 35 wt % based on the total weight of the pharmaceutical composition for appropriate tabletting and quality maintenance.

The binder refers to a material that offers materials in powder form adhesiveness and facilitates compression of the materials. The binder may be at least one selected from among starch, microcrystalline cellulose, highly dispersible silica, mannitol, lactose, polyethylene glycol, polyvinylpyrrolidone, cellulose derivatives (for example, hydroxypropyl methylcellulose, hydroxypropyl cellulose, or low-substituted hydroxypropyl cellulose), natural gum, synthetic gum, povidone, co-povidone, and gelatin, but is not limited thereto. In some embodiments, the binder may be used from about 2 wt % to about 15 wt % based on a total weight of the pharmaceutical composition for oral administration. In some other embodiments, the binder may be used from about 1 wt % to about 3 wt % based on the total weight of the oral pharmaceutical composition for appropriate tabletting and quality maintenance.

The disintegrant refers to a material added to facilitate disintegration or dissolution of a solid dosage form when administrated into a living body. The disintegrant may be starch, such as sodium starch glycolate, corn starch, potato starch, or pregelatinized starch, or modified starch; clay, such as bentonite, montmorillonite, or veegum; cellulose, such as microcrystalline cellulose, hydroxypropyl cellulose, or carboxymethyl cellulose; an algin, such as sodium alginate or alginic acid; a cross-linked cellulose, such as croscarmellose sodium; gum such as guar gum or xanthan gum; a cross-linked polymer such as cross-linked polyvinylpyrrolidone (crospovidone); or an effervescent agent such as sodium bicarbonate or citric acid, which may be used alone or as a mixture thereof, but is not limited thereto. In some embodiments, the disintegrant may be used from about 2 wt % to about 15 wt % based on a total weight of the pharmaceutical composition for oral administration. In some other embodiments, the disintegrant may be used from about 4 wt % to about 10 wt % based on the total weight of the oral pharmaceutical composition for appropriate tabletting and quality maintenance.

The glidant or lubricant refers to a material that prevents cohesion of powders to a compressing system and improves flowability of granules. The glidant may be hard anhydrous silicic acid, talc, stearic acid, a metal salt (magnesium salt, calcium salt, or the like) of stearic acid, sodium lauryl sulfate, hydrogenated vegetable oil, sodium benzoate, sodium stearyl fumarate, glyceryl behenate, glyceryl monostearate, or polyethylene glycol, which may be used alone or as a mixture thereof, but is not limited thereto. In some embodiments, the glidant may be used from about 0.1 wt % to about 5 wt % based on a total weight of the oral pharmaceutical composition. In some other embodiments, the glidant may be used from about 1 wt % to about 3 wt % based on the total weight of the oral pharmaceutical composition for appropriate tabletting and quality maintenance.

The adsorbent may be hydrated silicon dioxide, hard anhydrous silicic acid, colloidal silicon dioxide (Aerosil, available from Degussa), magnesium aluminometasilicate, microcrystalline cellulose, lactose, or a cross-linked polyvinylpyrrolidone, which may be used alone or as a mixture thereof, but is not limited thereto.

The stabilizer may be at least one selected from the group consisting of antioxidants, such as butylhydroxyanisole, butylhydroxytoluene, carotene, retinol, ascorbic acid, tocopherol, tocopherol polyethylene glycol succinic acid, or propyl gallate; cyclic sugar compounds such as cyclodextrin, carboxyethyl cyclodextrin, hydroxypropyl cyclodextrin, sulfobutyl ether, or cyclodextrin; and organic acids such as phosphoric acid, lactic acid, acetic acid, citric acid, tartaric acid, succinic acid, maleic acid, fumaric acid, glycolic acid, propionic acid, gluconic acid, or glucuronic acid, but is not limited thereto.

In some other embodiments, an additive known to improve the taste of by boosting a taste sense may be included. In some embodiments, a sweetener such as sucralose, sucrose, fructose, erythritol, acesulfame potassium, sugar alcohol, honey, sorbitol, or aspartame may be added to more effectively mask bitterness and maintain the stability and quality of the formulation. In some other embodiments, an acidifier such as citric acid or sodium citrate; a natural flavoring such as Japanese apricot flavor, lemon flavor, pineapple flavor, or herbal flavor; or a natural pigment such as natural fruit juice, chlorophyllin, or flavonoid may be used.

The pharmaceutical composition for oral administration may be a solid, semi-solid, or liquid dosage form acceptable for oral administration. Non-limiting examples of the oral solid dosage form are tablets, pills, hard or soft capsules, powders, fine granules, granules, powders for reconstitution of solution or suspension, lozenges, wafers, oral strips, dragees, or chewable gum, but are not limited thereto. Non-limiting examples of the oral liquid formulation are solution, suspension, emulsion, syrup, elixir, spirit, aromatic water, lemonade, extract, and tincture. Non-limiting examples of the semi-solid form are aerosol, cream, and gel.

In some embodiments, the pharmaceutical composition may be prepared as injections. In preparing the pharmaceutical composition as injections, a nontoxic buffer solution that is isotonic with blood may be further added as a diluent. An example of the nontoxic buffer solution is a phosphoric acid buffer solution at pH 7.4. The pharmaceutical composition may further include any other diluents or additives, in addition to the buffer solution.

A carrier for each of the above-listed dosage forms of the pharmaceutical composition and a method of preparing the same may be selected from those widely known in the art, for example, may be prepared according to a method described in the book entitled "Remington's Pharmaceutical Sciences (Newest edition)".

In some embodiments, a dose and administration time of the pharmaceutical composition for cancer treatment according to any of the above-described embodiments may vary depending on the age, gender, and body weight of a target subject, administration route, administration frequency, and form of medicine. A total daily dose of the pharmaceutical composition may be about 1 mg/kg to about 1000 mg/kg, and in some embodiments, about 0.01 mg/kg to about 100 mg/kg. The total daily dose of the pharmaceutical composition may be appropriately varied depending to the type of cancer, degree of cancer progression, administration route, and gender, age, and body weight of the target subject.

In some embodiments, to enhance radiotherapy effects in cancer treatment, the pharmaceutical composition for a radiation sensitizer for cancer treatment may be administered several times a day in a total daily dose of about 1 mg/kg to about 1000 mg/kg for adults as an effective component. The total daily dose of the pharmaceutical composition for a radiation sensitizer may be appropriately varied depending to the type of cancer, degree of cancer progression, administration route, and gender, age, body weight, health, or the like of the target subject.

In any of the pharmaceutical compositions for cancer treatment and the pharmaceutical compositions for a radiation sensitizer, according to the above-described embodiments of the present disclosure, the amount of the compound of Formula I may be in a range of about 0.0001 wt % to about 10 wt %, and in some embodiments, about 0.001 wt % to about 1 wt %, based on a total weight of the pharmaceutical composition.

One or more embodiments of the present invention will now be described in detail with reference to the following examples. However, these examples are only for illustrative purposes and are not intended to limit the scope of the one or more embodiments of the present invention.

Example 1

Preparation of Compound of Formula III

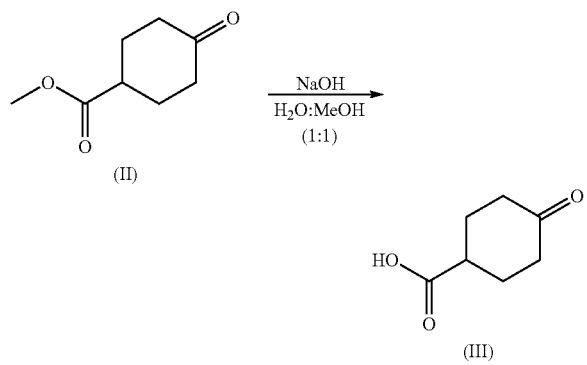

2.5 g (43.5 mmol) of a sodium hydroxide aqueous solution was added to a solution of 5.0 g (29.0 mmol) of ethyl-4-cyclohexanone carboxylate in methanol. The resulting reaction mixture was stirred at room temperature for reaction. After completion of the reaction, the solvent was removed under vacuum to obtain a crude product, which was then dissolved in water, and adjusted to a pH of 3 to 4 with hydrochloric acid, followed by extraction with ethyl acetate, drying with sodium sulfate ($Na_2SO_4$), and then concentration. The resulting crude product was purified using silica gel column chromatography to obtain 3.5 g of 4-cyclohexanone carboxylic acid in white solid as a compound of Formula III (Yield: 85%).

$^1$H NMR ($CDCl_3$, 400 MHz): δ10.50 (1H, s), 2.62-2.72 (1H, m), 2.30-2.10 (4H, m), 2.01-1.86 (4H, m); $^{13}$C NMR ($CDCl_3$, 100 MHz): δ210.8, 180.0, 44.5, 40.4 (20), 25.9 (2C).

Example 2

Preparation of Compound of Formula VI

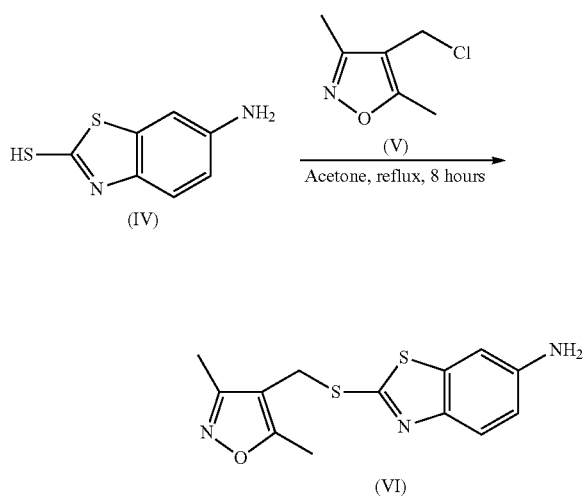

1.0 g (5.49 mmol) of 6-amino-2-mercapto benzothiazole (IV), 0.749 mL (6.04 mmol) of 4-(chloromethyl)-3,5-dimethylisooxazole (V), and 1.8 g (13.72 mmol) of $K_2CO_3$ were refluxed in acetone for about 8 hours. After completion of the reaction, the solvent was removed by rotary evaporation to obtain a crude product, which was then dissolved in water, followed by extraction with ethyl acetate, washing with sodium hydrogen carbonate, drying with sodium sulfate ($Na_2SO_4$), and then concentration. The resulting crude product was purified using silica gel column chromatography to obtain 1.07 g of a compound of Formula VI in white solid (Yield: 67%).

$^1$H NMR ($CDCl_3$, 400 MHz): δ 7.62 (1H, d, J=8.8 Hz), 6.93 (1H, d, J=2.0 Hz), 6.74 (1H, dd, J=2.4, 8.4 Hz), 4.21 (2H, s), 3.87 (2H, s), 2.34 (3H, s), 2.27 (3H, s); $^{13}$C NMR ($CDCl_3$, 100 MHz): δ164.2, 159.9, 158.9, 146.6, 143.5, 135.9, 122.6, 119.4, 114.1, 105.4, 100.5, 19.4, 11.0, 6.3.

Example 3

Preparation of Compound PB11 of Formula Ia

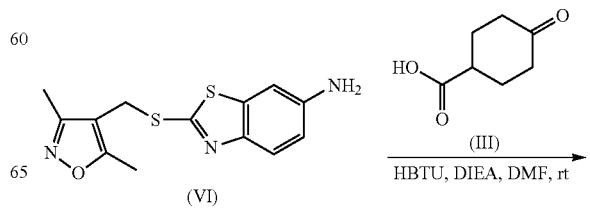

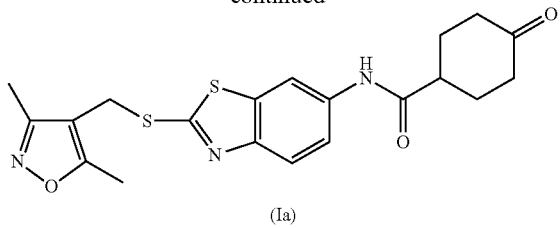

3.12 g (21.9 mmol) of 4-cyclohexanone carboxylic acid (III), 9.169 g (24.1 mmol) of HBTU, and 7.65 mL (43.8 mmol) of N,N-diisopropylethylamine (DIEA) were added to a solution of 6.4 g (21.9 mmol) of the amine compound of Formula VI in dimethylformate (DMF). The resulting reaction mixture was stirred at room temperature overnight. After removing DMF under vacuum, the residue was diluted in ethyl acetate, washed with sodium carbonate and then brine, dried using anhydrous sodium sulfate, and then filtered. After removing the solvent under vacuum, the resulting crude product was purified using silica gel column chromatography to obtain 7.0 g 4-oxo-cyclohexanecarboxylic acid [2-(3,5-dimethyl-isoxazole-4-yl)sulfanyl-benzothiazole-6-yl]-amide in white solid as a compound of Formula Ia (Yield: 77%).

$^1$H NMR (DMSO, 400 MHz): δ 10.23 (1H, s), 8.41 (1H, d, J=2.0 Hz), 7.80 (1H, d, J=8.8 Hz), 7.55 (1H, dd, J=2.0, 9.2 Hz), 4.38 (2H, s), 2.87-2.79 (1H, m), 2.49-2.10 (6H, m), 2.41 (3H, s), 2.24 (3H, s), 1.90 (2H, q, J=13.2 Hz); $^{13}$C NMR (DMSO, 100 MHz) δ 210.8, 173.0, 164.2, 159.9, 158.9, 149.1, 136.5, 135.3, 122.0, 119.4, 110.7, 100.5, 42.6, 40.0 (2C), 26.8 (2C), 19.4, 11.0, 6.3.

Example 4

Preparation of Compound PB12 of Formula Ib

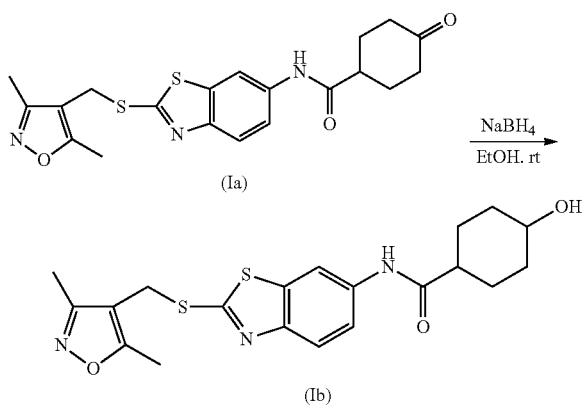

0.76 g (2.02 mmol) of NaBH$_4$ was added to a solution of 0.7 g (1.68 mmol) of the ketone derivative of Formula Ia (Example 3) in ethanol. The resulting reaction mixture was stirred at room temperature. After completion of the reaction, the reaction solvent was removed under vacuum to obtain a crude product. This crude product was dissolved in water, and pH-adjusted with 1N HCl to a pH 6 to 7. The resulting crude product was extracted with ethyl acetate, dried using sodium sulfate (Na$_2$SO$_4$), and then concentrated. The resulting crude product was purified using silica gel column chromatography to obtain 0.3 g of 4-hydroxy-cyclohexanecarboxylic acid [2-(3,5-dimethyl-isoxazole-4-yl)sulfanyl-benzothiazole-6-yl]-amide in white solid as a compound of Formula Ib (Yield: 43%).

$^1$H NMR (CD$_3$OD, 400 MHz): δ 8.25 (1H, d, J=2.0 Hz), 7.73 (1H, d, J=9.2 Hz), 7.47 (1H, dd, J=2.4, 8.8 Hz), 4.32 (2H, s), 3.96-3.94 (1H, m), 2.43-2.41 (1H, m), 2.39 (3H, s), 2.27 (3H, s), 2.06 (2H, q, J=12.8 Hz), 1.87-1.83 (2H, m), 1.66-1.56 (4H, m); $^{13}$C NMR (CD$_3$OD, 100 MHz) δ 173.0, 164.2, 159.9, 158.9, 149.1, 136.5, 135.3, 122.0, 119.4, 110.7, 100.5, 72.3, 43.5, 33.3 (2C), 23.1 (2C), 19.4, 11.0, 6.3.

Example 5

Preparation of Compound PB01 of Formula Ic

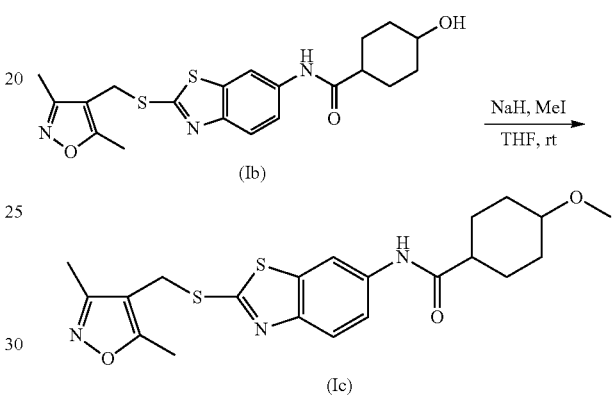

0.021 g (0.528 mmol) of NaH and 0.029 mL (0.48 mmol) of methyl iodide were added to a solution of 0.2 g (0.48 mmol) of the hydroxy derivative Formula Ib (Example 4) in THF. The resulting reaction mixture was stirred at room temperature. After completion of the reaction, the reaction solvent was removed by rotary evaporation, followed by dissolving the resulting mixture in water. The resulting mixture was extracted with ethyl acetate, washed with sodium hydrogen carbonate, dried using sodium sulfate (Na$_2$SO$_4$), and then concentrated. The resulting crude product was purified using silica gel column chromatography to obtain 0.080 g of 4-methoxy-cyclohexanecarboxylic acid [2-(3,5-dimethyl-isooxazole-4-yl)sulfanyl-benzothiazole-6-yl]-amide in white solid as a compound of Formula Ic (where R$^5$ is methyl) (Yield: 40%).

$^1$H NMR (CDCl$_3$, 400 MHz): δ 7.88 (1H, d, J=8.4 Hz), 7.58 (1H, d, J=2.4 Hz), 7.24 (1H, dd, J=2.4, 8.8 Hz), 4.36 (2H, s), 3.56-3.54 (1H, m), 3.26 (3H, s), 2.48 (3H, s), 2.34 (3H, s), 2.11-2.08 (1H, m), 1.92-1.53 (6H, m), 0.96 (2H, q, J=13.2 Hz); $^{13}$C NMR (CDCl$_3$, 100 MHz) δ 173.0, 164.2, 159.9, 158.9, 149.1, 136.5, 135.3, 122.0, 119.4, 110.7, 100.5, 84.1, 57.1, 43.5, 30.8 (2C), 23.4 (2C), 19.4, 11.0, 6.3.

Example 6

PPAR-γ Ligand Identification Test

The ability to induce adipogenesis of the compound PB11 of Example 3 and the compound PB01 of Example 5 was tested to identify whether the compounds PB11 and PB01 had activity of PPAR-γ ligands. 3T3-L1 cells (American Type Culture Collection, Manassas, Va.) were treated with 10 μM of the compounds PB11 or PB01 to induce adipogenesis. 3T3-L1 cells without any treatment, those treated with the same concentration of ciglitazone, and those treated with the same concentration of GW9662 (Cayman, Ann Arbor, Mich.) known as PPAR-γ ligand antagonist were used as control groups. After the induction of adipogenesis for about 48 hours, a degree of adipogenesis was identified by Oil-Red-O staining. The results are shown in FIG. 1.

FIG. 1 illustrates the results of imaging degrees of adipogenesis via Oil-Red-O staining after the treatment of 3T3-L1 cells with control compounds and 10 μM of the compounds PB01 or PB11 of Examples 3 and 5 for about 48 hours to induce adipogenesis.

As a result of the Oil-Red-O staining, the compound PB01 of Example 5 was found to have outstanding ability to induce adipogenesis, which is known as feature of PPAR-γ ligands. The compound PB11 of Example 3 was also found to have high activity in adipogenesis induction. These results indicate that the compounds PB01 and PB11 of Examples 5 and 3 were found to be PPAR-γ ligands.

Example 7

Evaluation of Cancer Cell Growth Inhibitory Effect

Cancer cell growth inhibitory effects of the compounds PB01 and PB11 of Examples 5 and 3 identified as PPAR-γ ligands were evaluated. Growth inhibitory effects of the compounds PB01 and PB11 of Examples 5 and 3 on various cancer cells, including human non-small cell lung cancer cell strains (A549, H460), breast cancer cell strains (MCF-7, T-470), colorectal cancer cell strains (LoVo, SW480), and leukocytes cancer cell strains (HL-60, K562) (American Type Culture Collection, Manassas, Va.), were evaluated using WST-1 method. About $5 \times 10^3$ cells per well of each type of cancer cell strains were portioned into a 96-well plate, and incubated with different concentrations of each of the compounds PB01 and PB11 of Examples 5 and 3 in 200 ul of a culture solution for 24 hours, 48 hours, and 72 hours. After the incubation for the different durations, 10 ul of a WST-1 solution was added to each well, followed by incubation at about 37° C. for about 1 hour. Absorbance at 450 nm was measured to determine cell viability. The results are shown in FIGS. 2A to 2F.

Figure 2A:
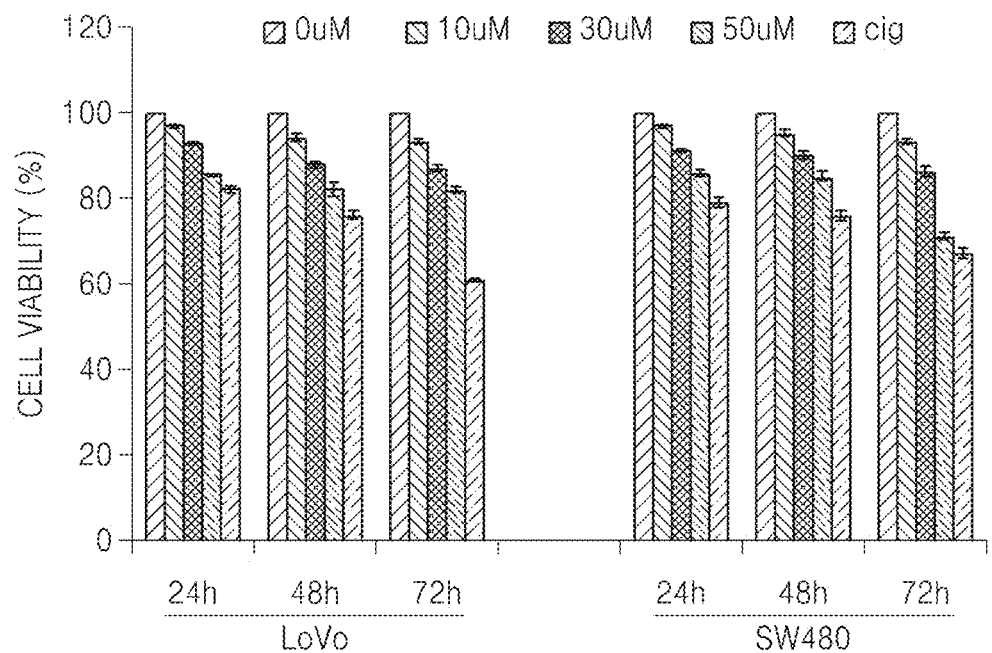
FIG. 2A to FIG. 2C illustrate the results of measuring cell viability by WST-1 method after incubation of various cancer cell strains with the compound PB01 of Example 5.
Figure 2A:
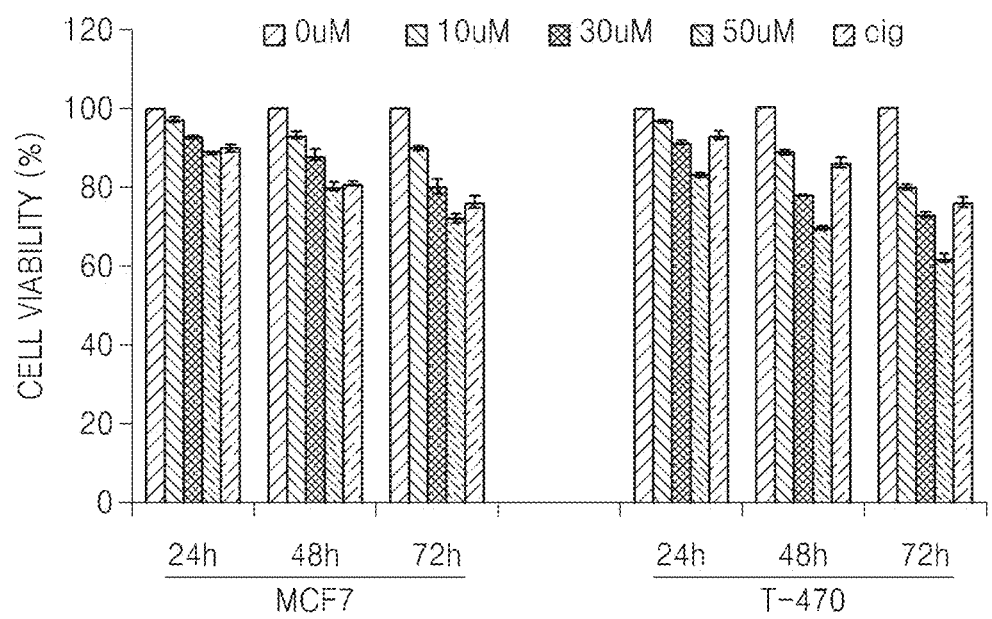
Figure 2B:
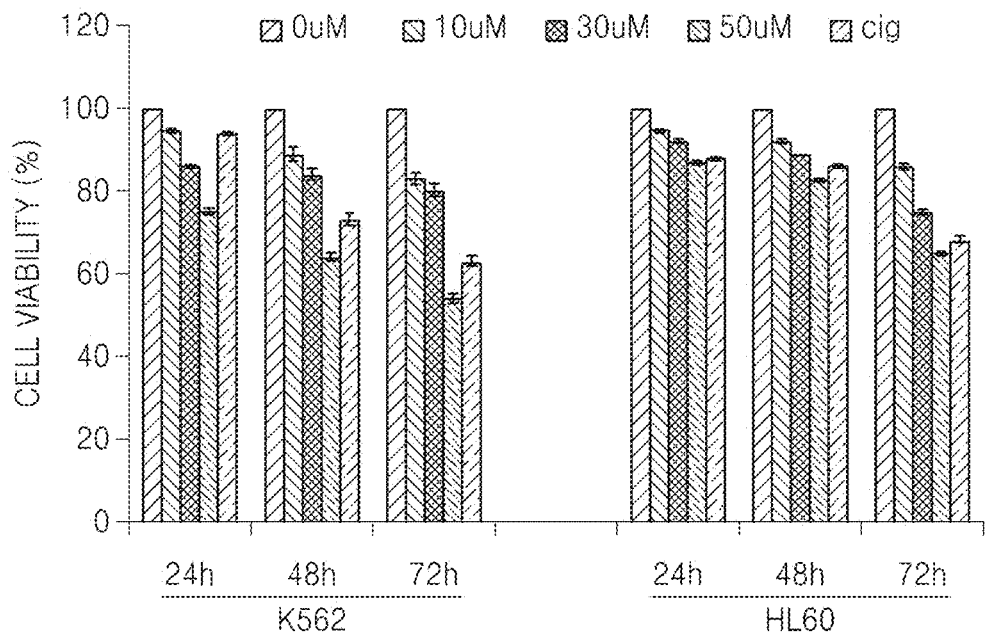
Figure 2B:
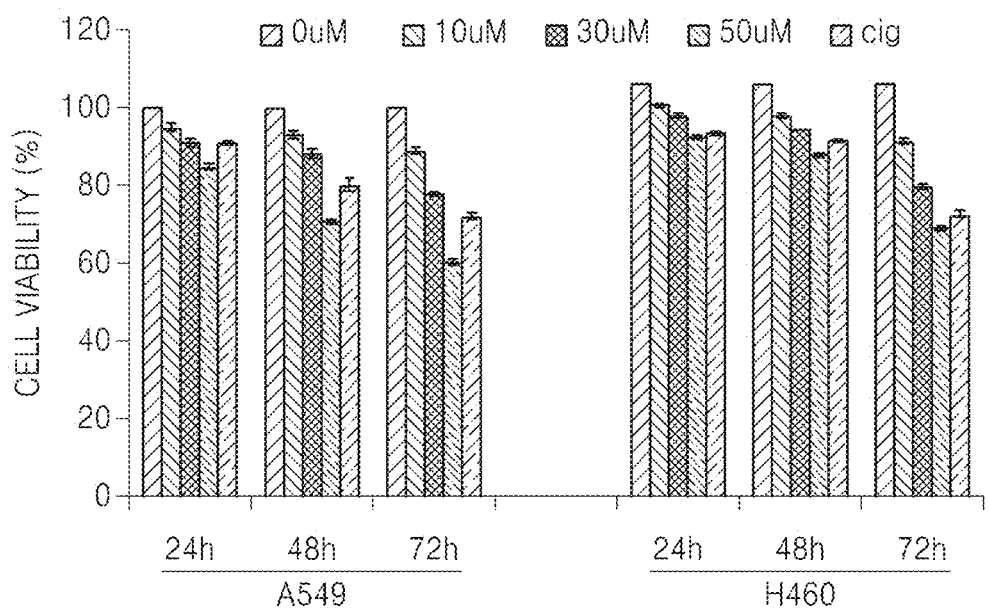
Figure 2C:
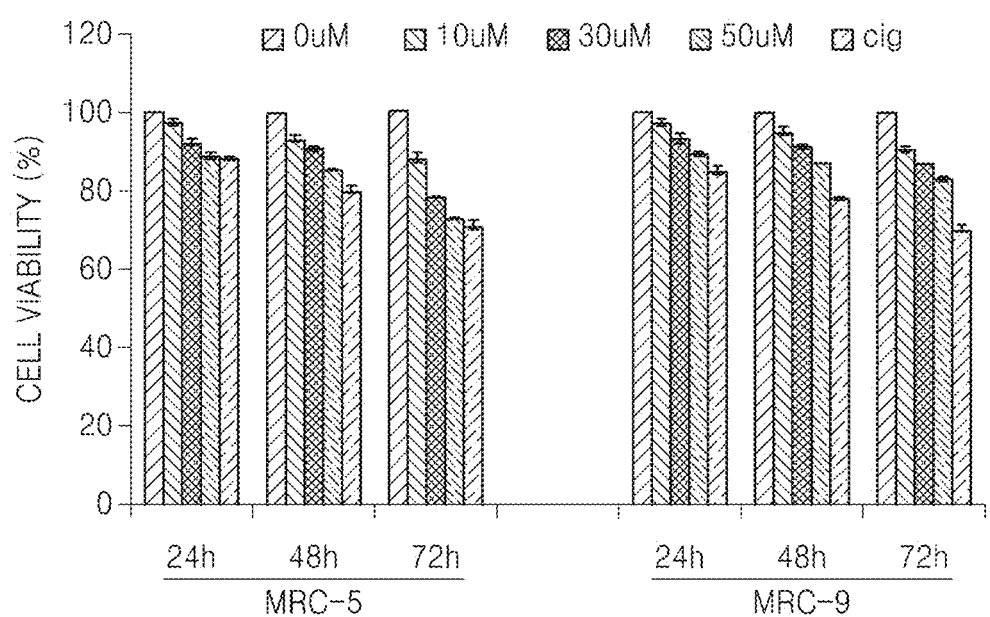

FIGS. 2A to 2C illustrates the results of measuring cell viability by WST-1 method after the incubation of various cancer cell strains with the compound PB01 of Example 5.

Figure 2D:
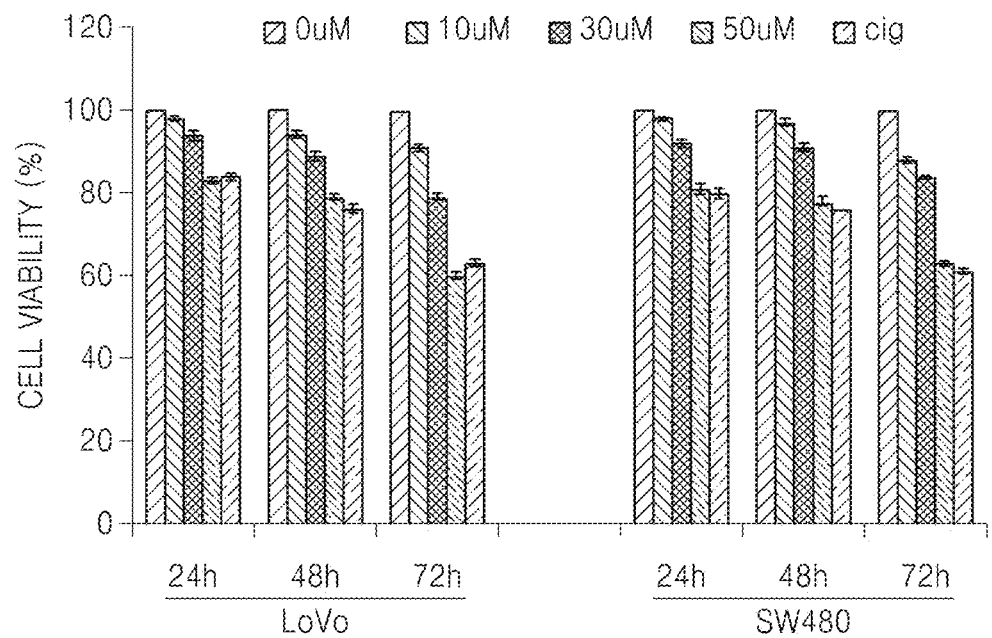
FIG. 2D to FIG. 2F illustrate the results of measuring cell viability by WST-1 method after incubation of various cancer cell strains with the compound PB11 of Example 3.
Figure 2D:
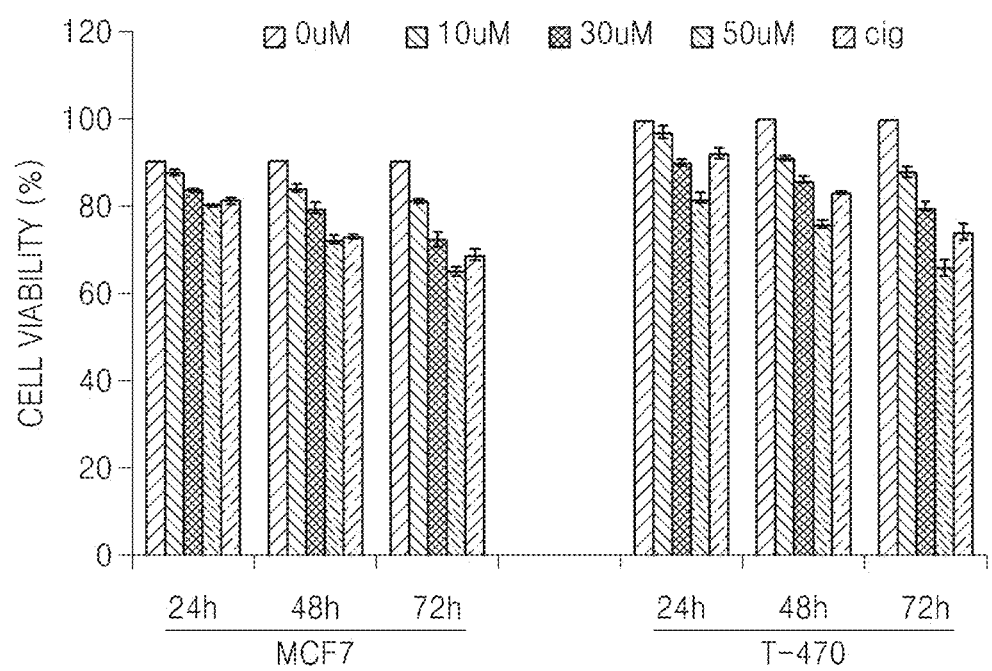
Figure 2E:
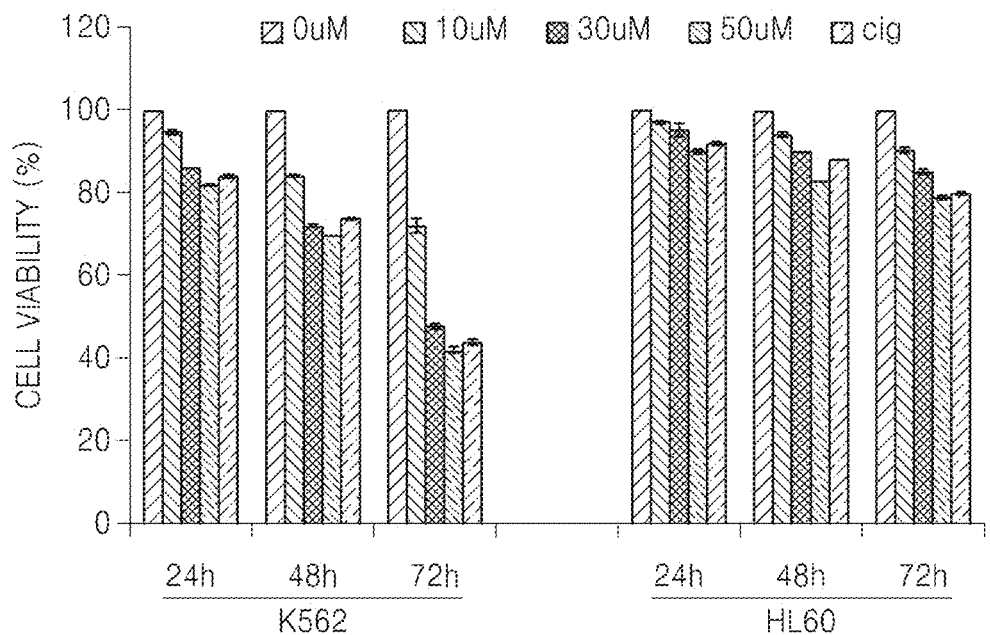
Figure 2E:
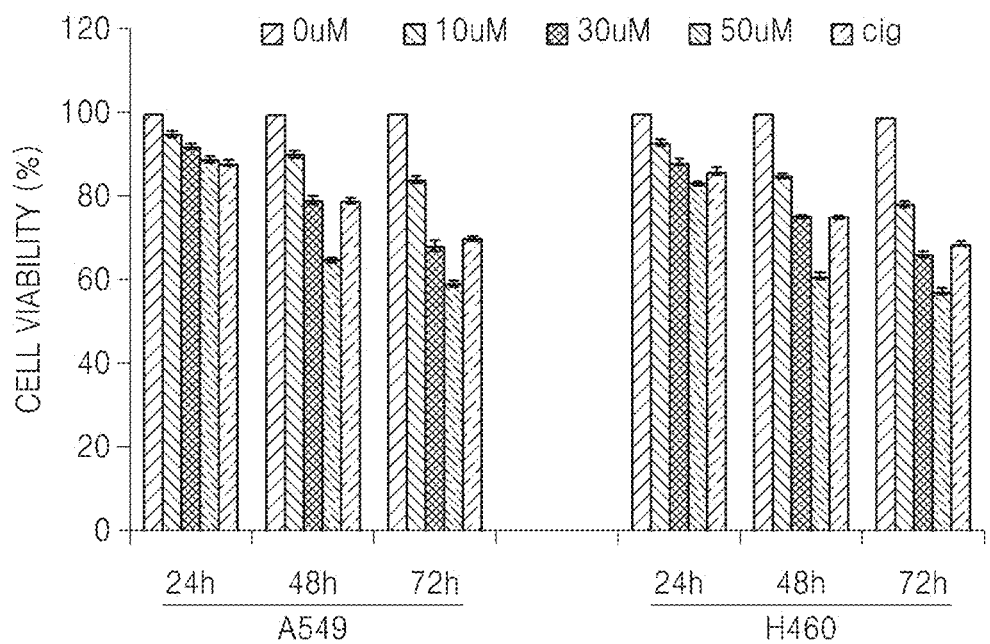
Figure 2F:
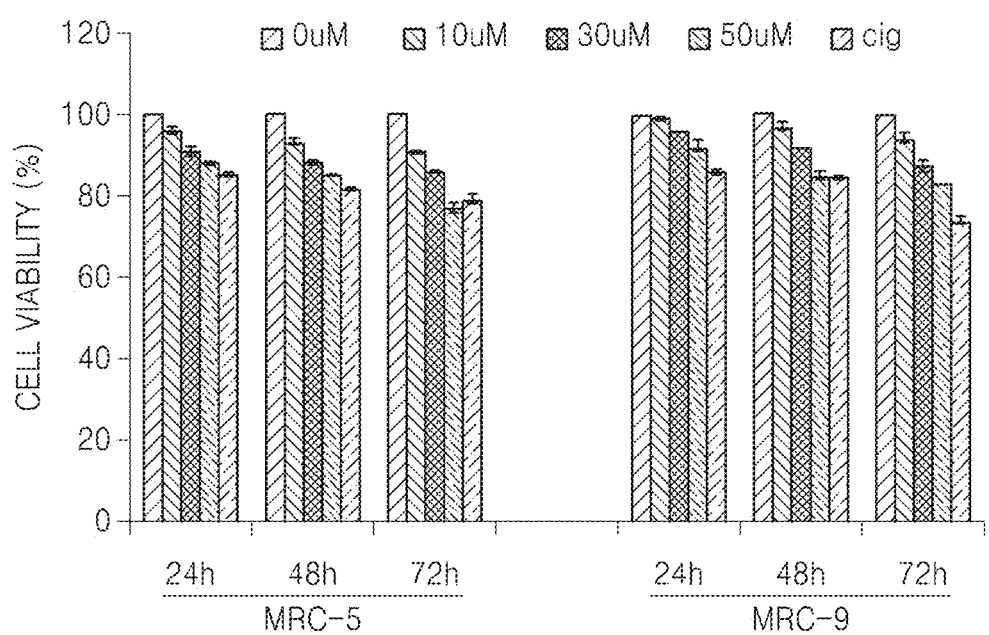

FIGS. 2D to 2F illustrates the results of measuring cell viability by WST-1 method after the incubation of various cancer cell strains with the compound PB11 of Example 3.

The growth inhibitory effects of the compounds PB01 and PB11 on various cancer cell strains were found to be prominent at a concentration of 50 μM. Even though the sensitivity of the compounds PB01 and PB05 slightly differs among the different cancer cell strains, the compounds PB01 and PB05 were the most effective in inhibiting cancer cell growth in the human non-small cell lung cancer cell strains A549 and H460, but had nearly zero cancer cell growth inhibitory effect in non-cancer lung cell strains MRC-5 and MRC-9, indicating that the compounds PB01 and PB11 of Examples 5 and 3 have a cell growth inhibitory effect selectively only on cancer cell strains.

Example 8

Apoptosis Effect Assay on Non-Small Cell Lung Cancer Cell Strain

Whether the cancer cell growth inhibitory effects of the compounds PB01 and PB11 on the non-small cell lung cancer cell strains is associated with apoptosis was investigated. The cell growth inhibitory effects were evaluated by a trypan blue assay, and cell shapes were observed using an inverted microscope. The shapes of cell nuclei were observed via Hoeschst 33342 staining. Degrees of inducing apoptosis were quantized by flow cytometry (fluorescent activated cell sorting (FACS)).

As a result, $IC_{50}$s of the compounds PB01 and PB11 in the human nonsmall cell lung cancer cell strains A549 and H460 were 50 μM, and the time taken to reach the $IC_{50}$s was 48 hours. Both of the compounds PB01 and PB11 were found to induce cell death in lung cancer cells, indicating that the compounds PB01 and PB11 may induce apoptosis as a cell death mechanism.

1) Evaluation of Apoptosis Effect of PB01 and PB11 in Non-Small Cell Lung Cancer Cells After about $5 \times 10^3$ cells per well of each of the human non-small cell lung cancer cell strains A549 and H460 were portioned into a 96-well plate, about 10 uM to about 50 uM of the compounds PB01 or PB11 in 200 ul of culture solution were added into the wells, and incubated for about 8 to 72 hours. Cells were collected from the incubation product, and centrifuged at about 2,000 rpm for 5 minutes. After removing a supernatant, the remaining cells were mixed with 1 mL of phosphate-buffered saline (PBS) to obtain a cell suspension, which was then mixed with an equal amount of 0.5% trypan blue (Gibco BRL), followed by treatment for about 1 minute. The number of live cells was counted using a phase-contrast) microscope. The live cell counting was repeated three times, and an average live cell count and a standard error were calculated using a Microsoft Excel program. Cell viability graphs with respect to compound concentration and incubation time were obtained. The same experiment was performed with 50 μM of the compound PB01, PB11 50 μM of the compound PB11, or 150 μM of the compound PB12 150 μM, and cell viability graphs with respect to compound concentration and incubation time were obtained.

Figure 3A:
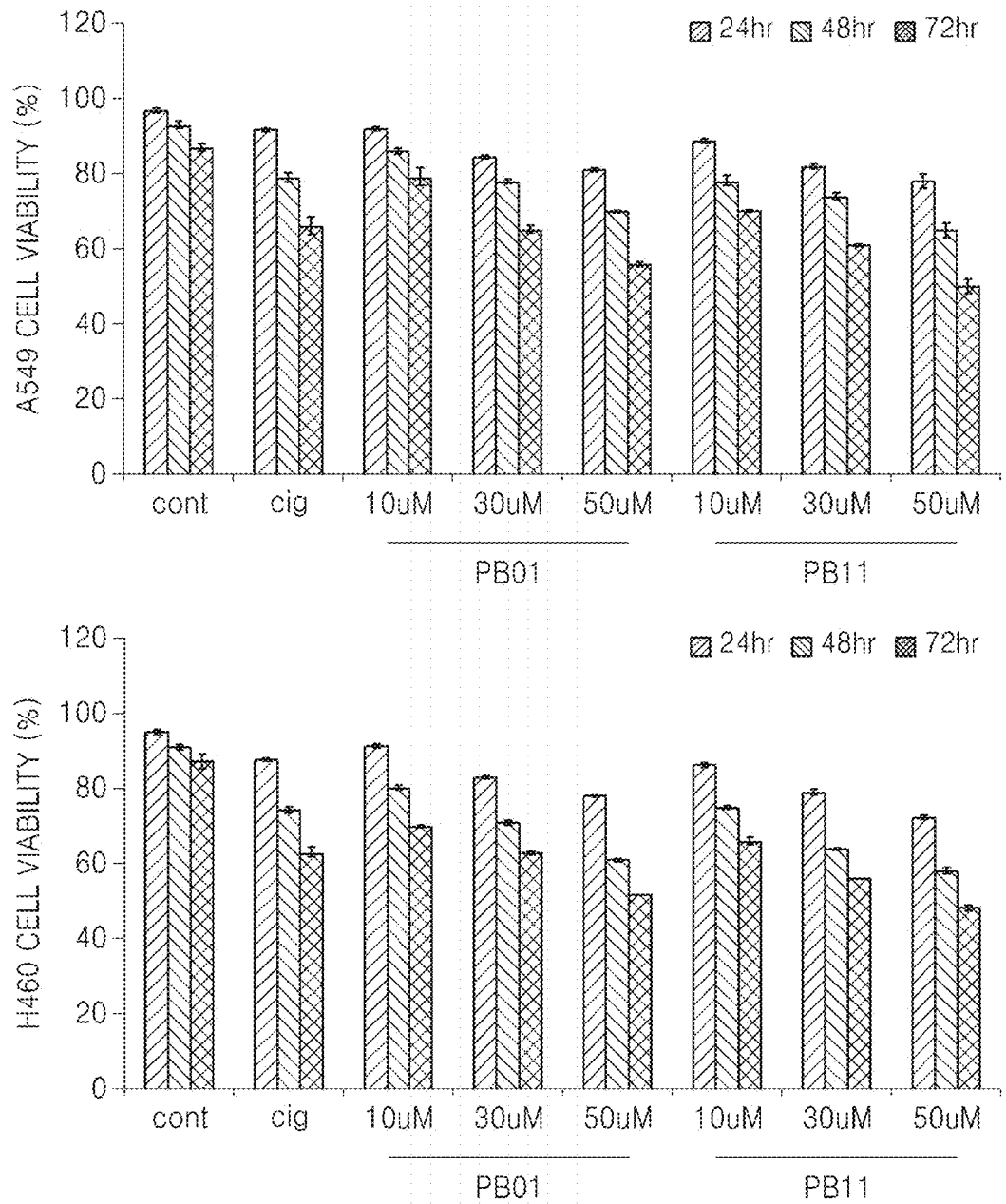
FIG. 3A illustrates graphs of cell viability with respect to test compound concentration and incubation time in non-small cell lung cancer cell strains A549 and H460 after incubation together with the compounds PB01 or PB 11 of Examples 5 and 3, obtained by microscopy with trypan blue staining.

FIG. 3A illustrates graphs of cell viability with respect to test compound concentration and incubation time in the non-small cell lung cancer cell strains A549 and H460 after incubation together with the compounds PB01 or PB 11 of Examples 5 and 3, obtained by microscopy with trypan blue staining.

Figure 3B:
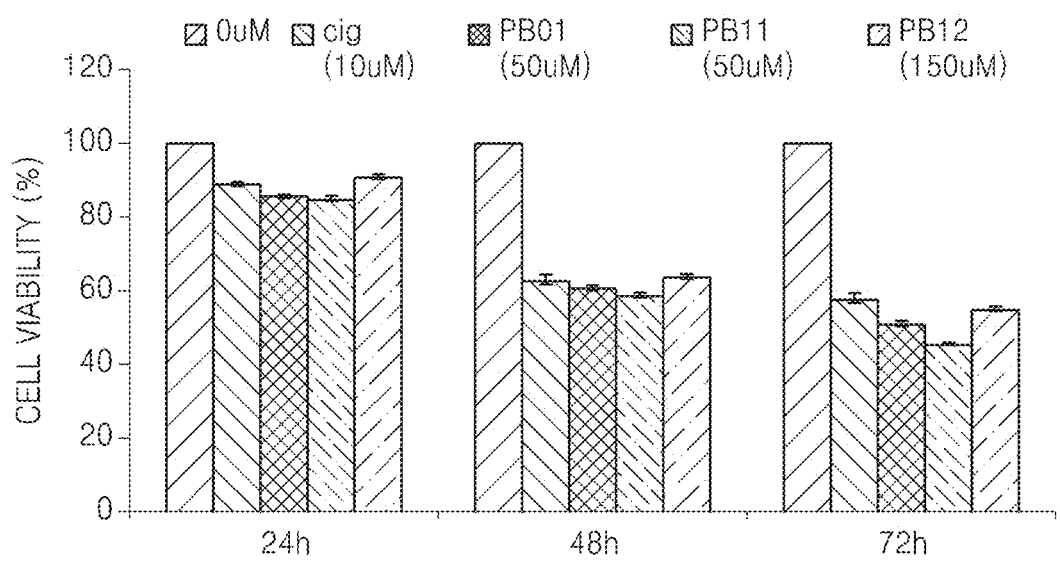
FIG. 3B illustrates graphs of cell viability with respect to test compound concentration and incubation time in the non-small cell lung cancer cell strain H460 after incubation together with the compounds PB01, PB 11, or PB12 of Examples 5, 3, and 4, obtained by microscopy with trypan blue staining.

FIG. 3B illustrates graphs of cell viability with respect to test compound concentration and incubation time in the non-small cell lung cancer cell strain H460 after incubation together with the test compounds PB01, PB 11, or PB12 of Examples 5, 3, and 4, obtained by microscopy with trypan blue staining.

Referring to FIGS. 3A and 3B, the compounds PB01, PB 11, and PB12 of Examples 5, 3, and 4 were found to have improved cancer cell apoptosis effects with increases in concentration and incubation time. In particular, remarkable cancer cell apoptosis effects were obtained in the groups treated with 50 μM of the compound PB01 or the compound PB11.

After the incubation along with 50 μM of the compounds PB01 or PB11 for 48 hours, morphological changes in the non-small cell lung cancer cell strain H460 were observed using an inverted microscope at a magnification of 200×. The results are shown in FIG. 4.

Figure 4:
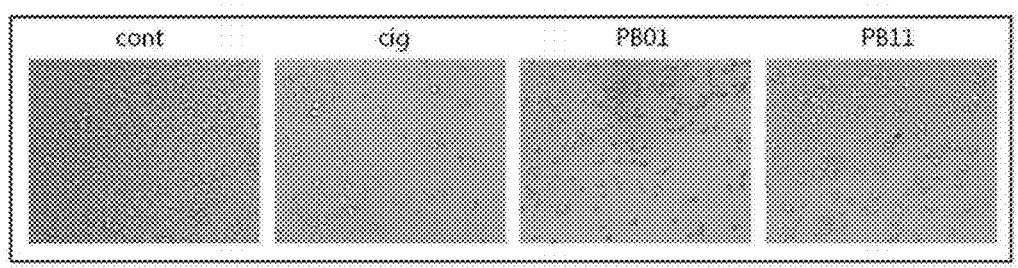
FIG. 4 illustrates microscopic images of the non-small cell lung cancer cell strain H460 after incubation with 50 μM of the compounds PB01 or PB11 of Examples 3 and 5 for about 48 hours, obtained using an inverted microscope at a magnification of 200×.

Referring to FIG. 4, when treated with the compounds PB01 or PB11 of Examples 5 and 3, the cancer cells appear to lose adhesion with reduced density, and float on the surface of the medium. This morphological change seems to coincide with the cell growth inhibitory effects of the compounds PB01 and PB11.

2) Observation on Nuclear Agglutination and Segmentation in Non-Small Cell Lung Cancer Cells by PB01 and PB11

To observe typical nuclear morphological changes from cell death, the cells treated with the compounds PB01 or PB11 of Examples 5 and 3 were collected, followed by removing a supernatant. After 500 µl of a fixing solution as a 1:9 mixture of a 37% formaldehyde solution and PBS buffer solution was added into the remaining cells, thoroughly mixed together, and left at room temperature for about 10 minutes for fixation. After the fixed cells were centrifuged at about 2,000 rpm for about 5 minutes, the fixing solution was removed, and the remaining cells were floated in a PBS buffer solution. After dropping the floating cells onto a slide glass, followed by cytospinning at about 1,000 rpm for about 5 minutes to fix the floating cells onto the slide glass. The slide glass with the fixed cells was treated with 2 µg/mL of a Hoechst 33342 solution (Sigma, St. Louis, Mo., U.S.A), followed by staining at room temperature for about 20 minutes. After termination of the staining, the staining reagent was washed out, and nuclear morphological changes in the cancer cells were observed by florescent microscopy (ECLIPSE E600; Nikon, Tokyo, Japan) at a 400× magnification. The results are shown in FIGS. 5 and 6.

Figure 5:
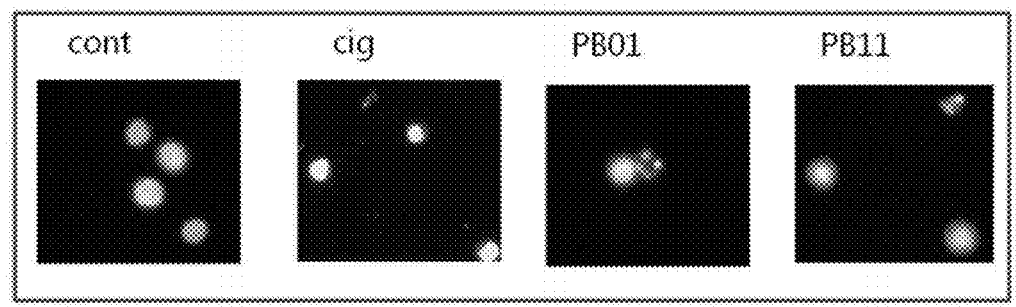
FIG. 5 illustrates fluorescent microscopic images of the non-small cell lung cancer cell strain H460 at a 400× magnification obtained via Hoechst staining after incubation with 50 uM of the compounds PB01 or PB11 of Examples 5 and 3 for about 48 hours in order to observe nuclear morphological changes in the cancer cells.

FIG. 5 illustrates fluorescent microscopic images of the non-small cell lung cancer cell strain H460 at a 400× magnification obtained via Hoechst staining after incubation with 50 uM of the compounds PB01 or PB11 of Examples 5 and 3 for about 48 hours in order to observe nuclear morphological changes in the cancer cell.

Figure 6:
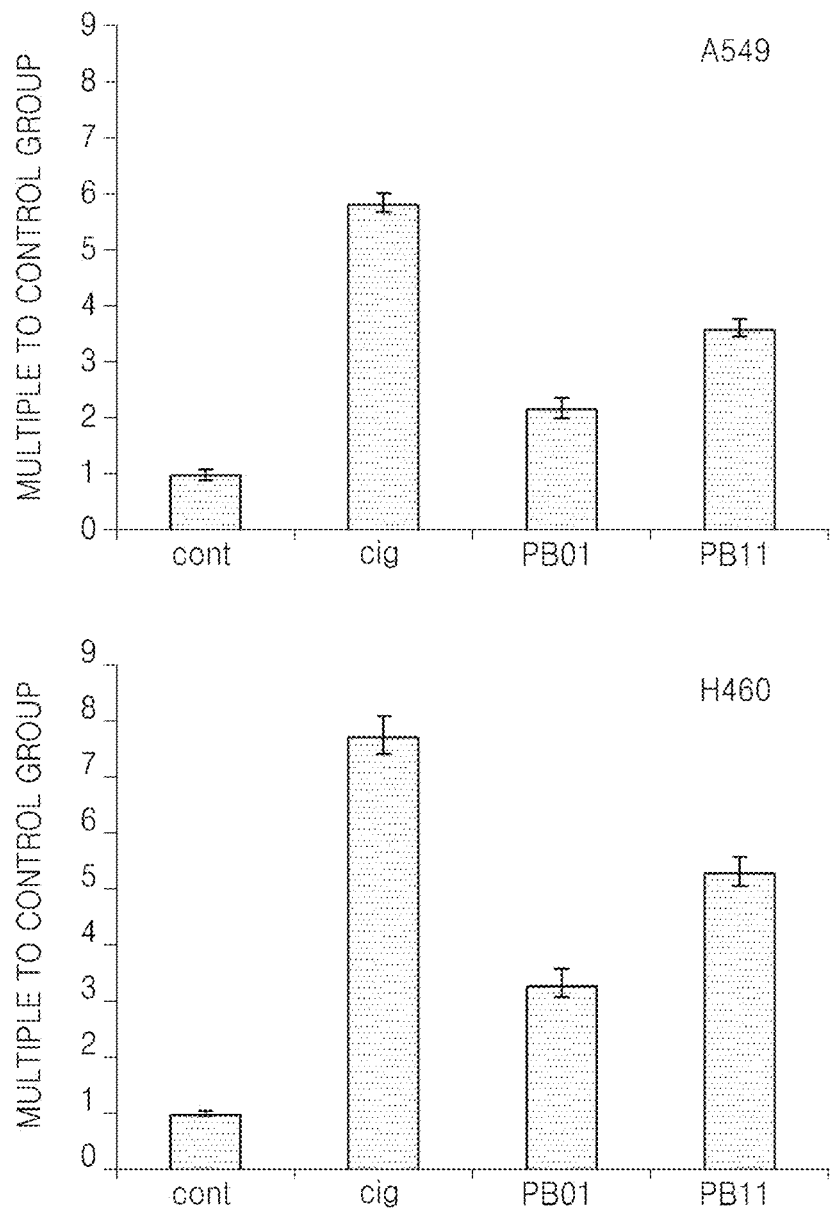
FIG. 6 illustrates graphs of degrees of nuclear agglutination and segmentation, obtained based on the nuclear morphological changes in the non-small cell lung cancer cell strain A549 or H460 that were observed by fluorescent microscopy at a 400× magnification via Hoechst staining after incubation with 50 uM of the compound PB01 or PB11 of Examples 5 and 3 for about 48 hours.

FIG. 6 illustrates graphs of degrees of nuclear agglutination and segmentation, obtained based on the nuclear morphological changes in the non-small cell lung cancer cell strain A549 or H460 that were observed by fluorescent microscopy at a 400× magnification via Hoechst staining after incubation with 50 uM of the compound PB01 or PB11 of Examples 5 and 3 for about 48 hours.

Referring to FIGS. 5 and 6, in the cancer cells grown in a normal medium normally stained nuclei appeared distinct. However, in the cancer cells treated with the compounds of PB01 or PB11 of Examples 5 and 3, increased apoptotic bodies due to nuclear agglutination were found, which is a typical feature observed in cells with apoptosis. These results indicate that cell growth inhibitory effects and morphological changes in the non-small cell lung cancer cells treated with the compounds PB01 and PB11 are related with apoptosis.

3) Measurement of LDH Release from Non-Small Cell Lung Cancer Cells Treated with PB01 or PB11

After incubation of the non-small cell lung cancer cell strains A549 and H460 treated with the compound PB01 or PB11 for 8, 24, and 48 hours, only supernatants were recovered the culture products. The activity of lactate dehydrogenase (LDH) may be measured by detecting an amount of LDH released from the cell cytosol with a Cytotoxicity Detection Kit (available from Roche Applied Science, Indianapolis, Ind.). The amounts of LDH release induced by the compound PB01 or PB11 were calculated as a percentage amount of extracellular LDH released from the cells with respect to a total amount of LDH as a sum of the extracellular released LDH and the intracellular LDH remaining in the cells. The results are shown in FIG. 7.

Figure 7:
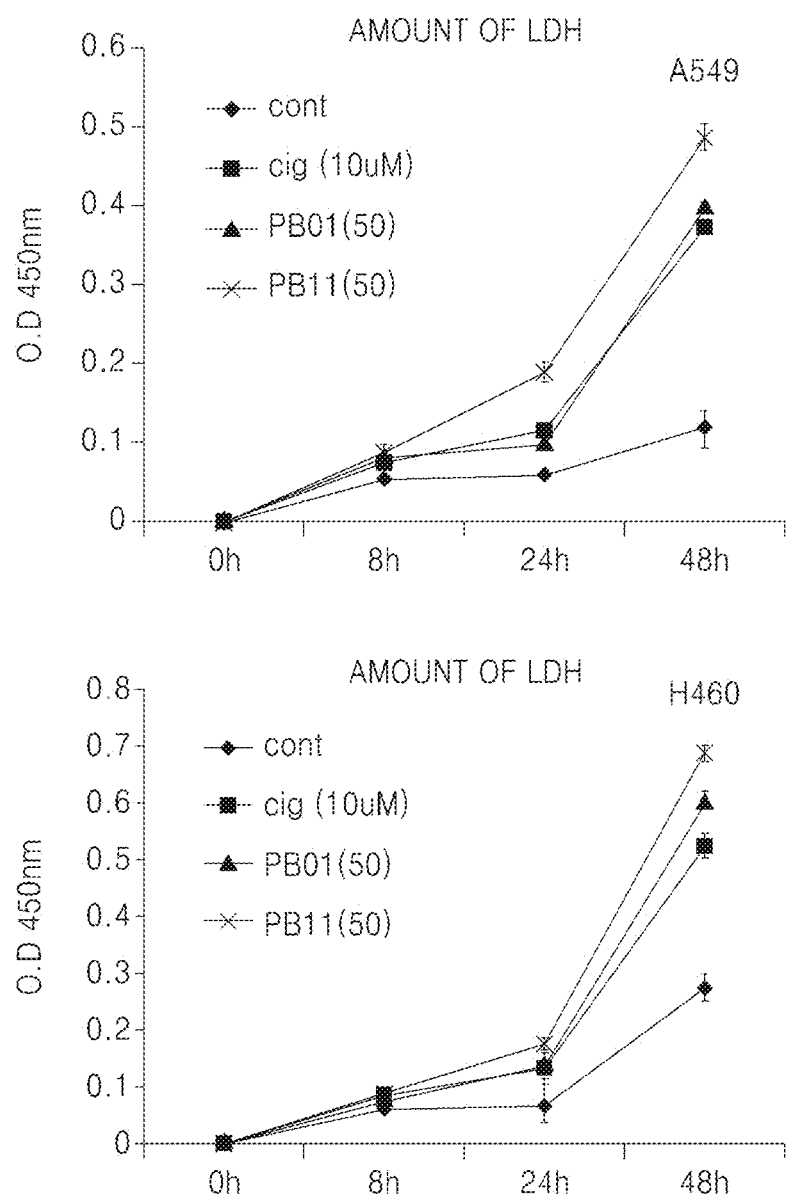
FIG. 7 illustrates graphs of amount of lactate dehydrogenase (LDH) released from the non-small cell lung cancer cell strains A549 and H460 treated with 50 uM of the compound PB01 or PB11 of Examples 5 and 3 into culture media while incubation for 0 to 48 hours.

FIG. 7 illustrates graphs of amount of LDH released from the non-small cell lung cancer cell strains A549 and H460 treated with 50 uM of the compound PB01 or PB11 of Examples 5 and 3 into the culture media while incubation for 0 to 48 hours.

Referring to FIG. 7, in the groups (the non-small cell lung cancer cells A549 and H460) treated with the compound PB01 or PB11, the amounts of extracellular LDH released from the cells were increased with time, compared to the untreated groups, indicating that a cell depth mechanism in the groups treated with the compound PB01 or PB11 occurred through apoptosis.

Example 9

Investigation on Cell Death Mechanism in Non-Small Cell Lung Cancers

1) Measurement of Effects of PB01 and PB11 on Sub-G1 Phase Cell Number

After incubation of the non-small cell lung cancer cells A549 and H460 treated with 50 µM of the compound PB01 or PB11 of Examples ?5 and 3 for 48 hours, the non-small cell lung cancer cells A549 and H460 were collected and floated with a 1×PBS (pH 7.4), followed by fixing at about −20° C. with a 70% cold ethanol, washing twice with a 1×PBS, and then staining with 10 µg/mL of propidium iodide (including 0.5% of PI, Tween-20, 100 µg/mL of 0.1% RNase) at room temperature for about 30 minutes. The stained cells were analyzed by flow cytometry with a FACScan™ (available from Becton Dicknson). The results are shown in FIG. 8.

Figure 8A:
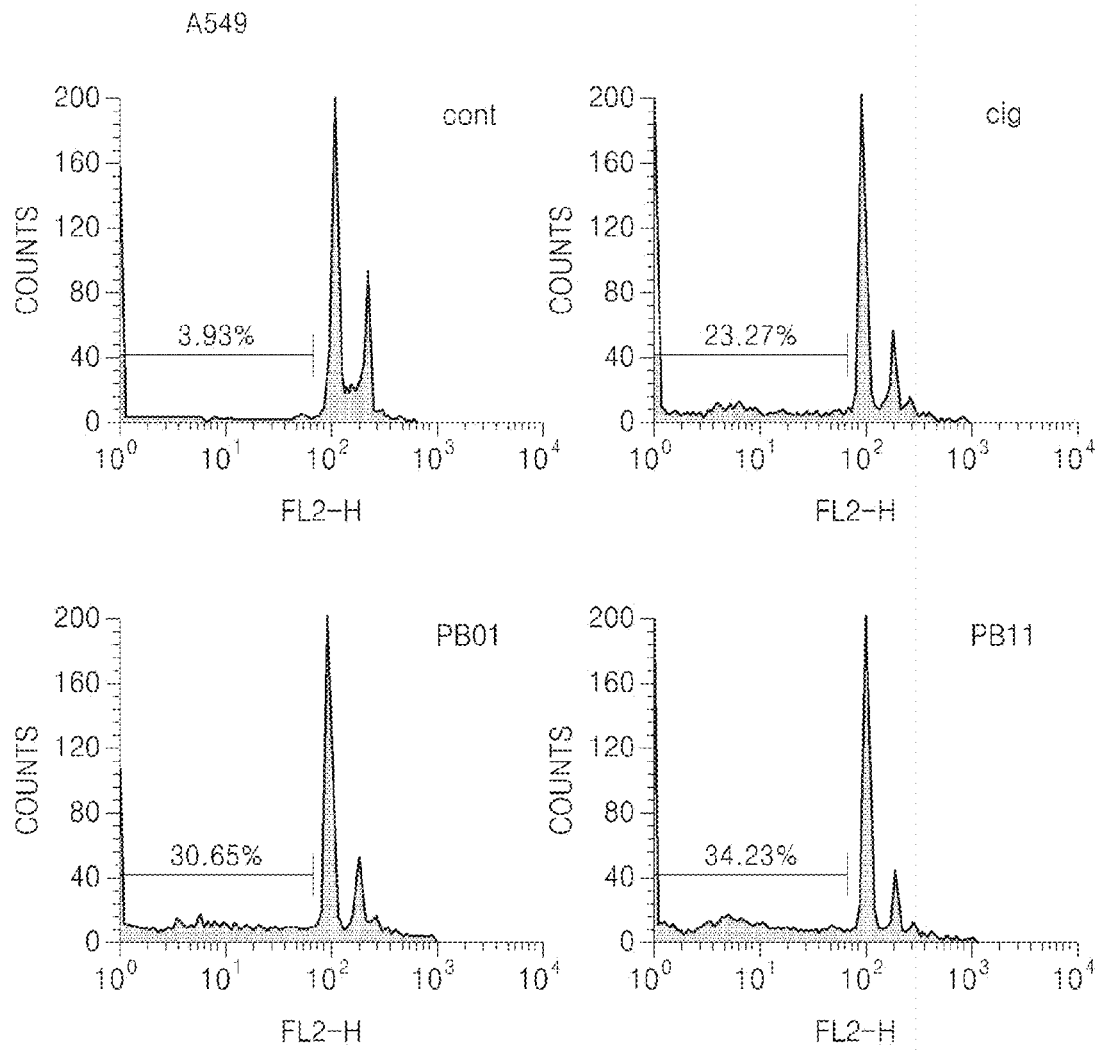
FIG. 8A illustrates the results of flow cytometry on the non-small cell lung cancer cells A549 after incubation with 50 μM of the compounds of PB01 or PB11 of Examples 5 and 3 for 48 hours, followed by staining with propidium iodide.

FIG. 8A illustrates the results of flow cytometry on the non-small cell lung cancer cells A549 after incubation with 50 µM of the compound of PB01 or PB11 for 48 hours, followed by staining with propidium iodide.

Figure 8B:
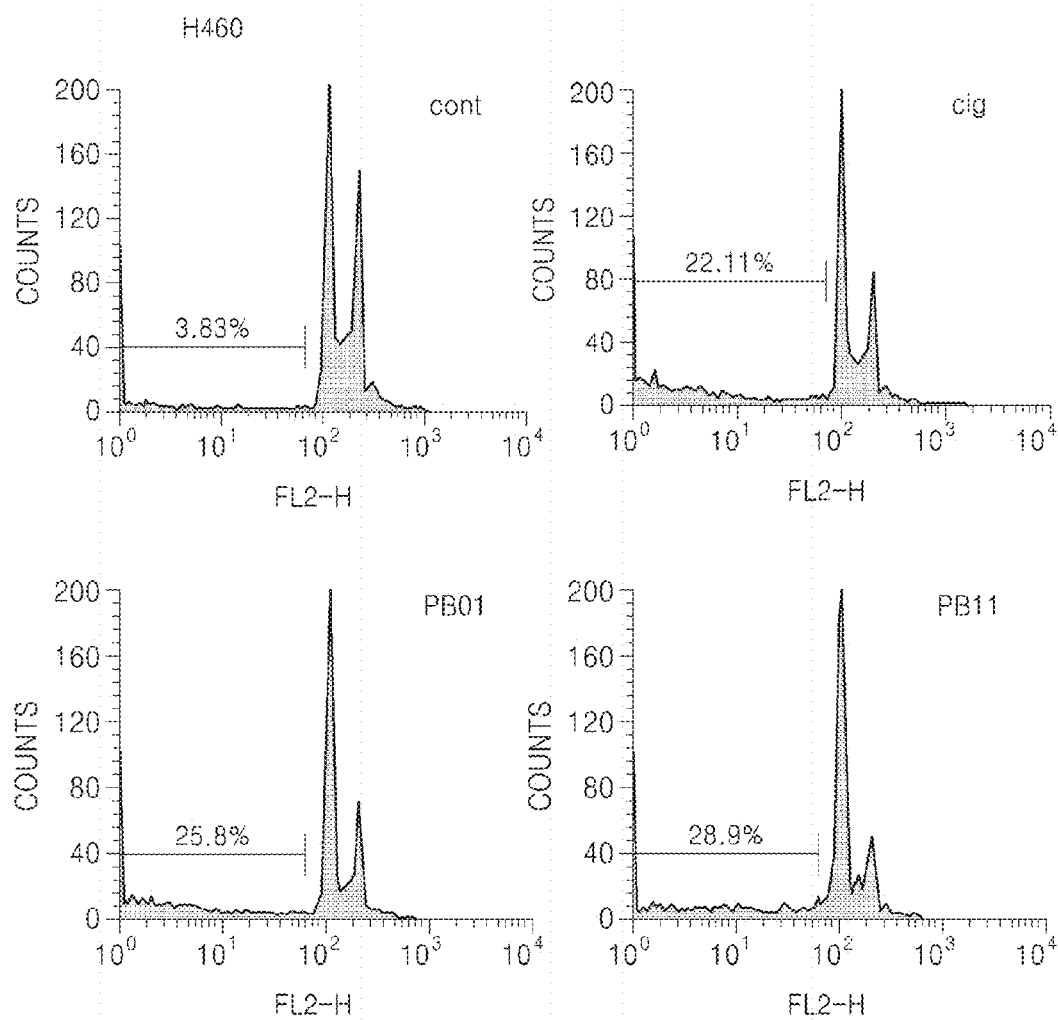
FIG. 8B illustrates the results of flow cytometry on the non-small cell lung cancer cells H460 after incubation with 50 μM of the compounds of PB01 or PB11 of Examples 5 and 3 for 48 hours, followed by staining with propidium iodide.

FIG. 8B illustrates the results of flow cytometry on the non-small cell lung cancer cells H460 after incubation with 50 µM of the compound of PB01 or PB11 for 48 hours, followed by staining with propidium iodide.

Referring to FIG. 8, a sharp increase in the number of sub-G1 phase cells occurred in the non-small cell lung cancer cells A549 and H460 treated with 50 µM of the compounds of PB01 or PB11, indicating that cell death occurs through apoptosis.

2) Measurement of Dead Cell Count in Non-Small Cell Lung Cancer Cells Treated with PB01 or PB11

About $5 \times 10^5$ cells per well of each of the non-small cell lung cancer cell strains A549 and H460 were portioned into a 6-well plate and then incubated with the compounds PB01 or PB11 for about 40 hours in the same manner as described above. A cell layer was washed with PBS and then treated with trypsin-EDTA solution to isolate cells. The isolated cells were collected and stained with an Annexin V Flous Staining kit (available Roche Applied Science, Penzberg, Germany) in a dark condition for about 30 minutes. The stained cells were analyzed by flow cytometry using a FACScan™ (available from Becton Dicknson) to count the number of dead cells and then calculate an apoptosis ratio. The same experiment was performed with 50 µM of PB01, 50 µM of PB11, or 150 µM of PB12 in the same manner as described above. The graphs of cell viability with respect to compound concentration and incubation time obtained based on the experimental results are shown in FIGS. 9A and 9B.

Figure 9A:
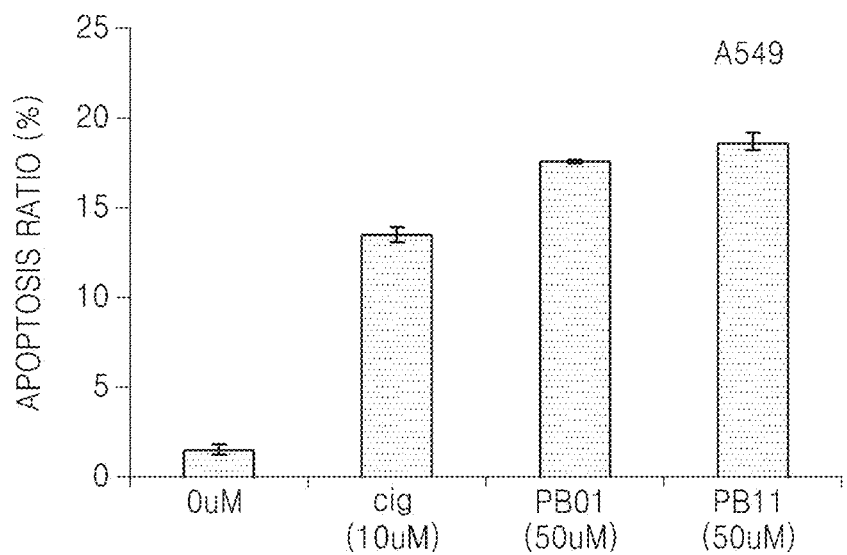
FIG. 9A illustrates graphs of apoptosis ratio in the non-small cell lung cancer cell strains A549 and H460 incubated with 50 μM of the compounds PB01 or PB11 of Examples 5 and 3 for about 40 hours, wherein the apoptosis ratios were calculated based on the results of flow cytometry using FACScan™ (available Becton Dicknson) via staining with an Annexin V Flous Staining kit in a dark condition for about 30 minutes.
Figure 9A:
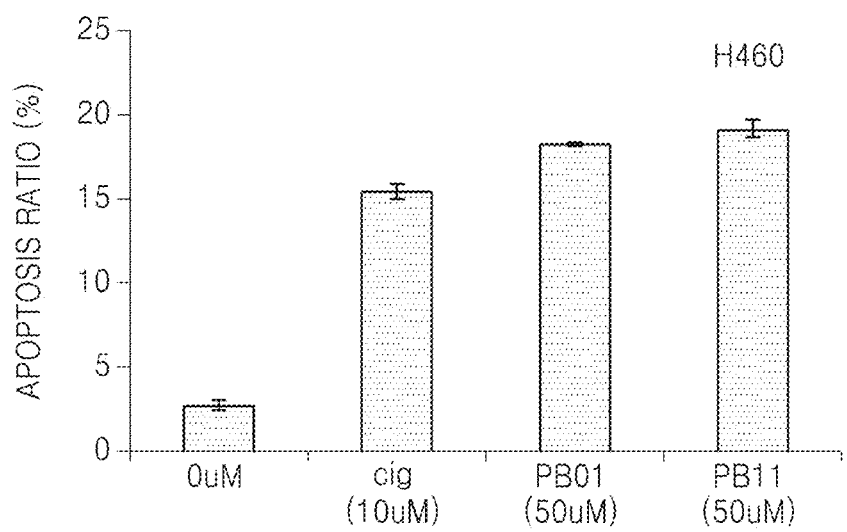

FIG. 9A illustrates graphs of apoptosis ratio in the non-small cell lung cancer cell strains A549 and H460 incubated with 50 µM of the compounds PB01 or PB11 of Examples 5 and 3 for about 40 hours, wherein the apoptosis ratios were calculated based on the results of flow cytometry using FACScan™ (available Becton Dicknson) via staining with an Annexin V Flous Staining kit in a dark condition for about 30 minutes.

Figure 9B:
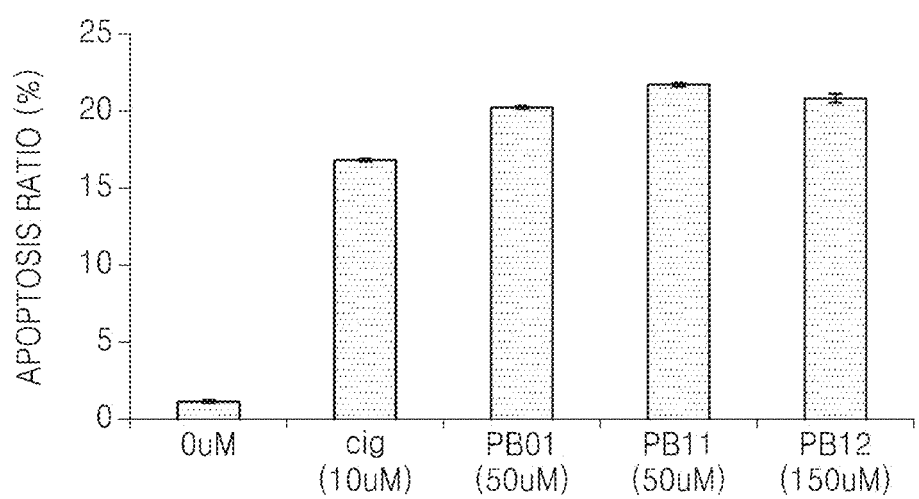
FIG. 9B illustrates graphs of apoptosis ratio in the non-small cell lung cancer cell strain H460 incubated with the compounds PB01, PB11, or PB12 of Examples 5, 3, and 4 for about 40 hours, wherein the apoptosis ratios were calculated based on the results of flow cytometry using FACScan™ (available Becton Dicknson) via staining with an Annexin V Flous Staining kit in a dark condition for about 30 minutes.

FIG. 9B illustrates graphs of apoptosis ratio in the non-small cell lung cancer cell strain H460 incubated with the compound PB01, PB11, or PB12 for about 40 hours, wherein the apoptosis ratios were calculated based on the results of flow cytometry using FACScan™ (available Becton Dicknson) via staining with an Annexin V Flous Staining kit in a dark condition for about 30 minutes.

Referring to FIGS. 9A and 9B, the compounds PB01, PB11, and PB12 of Examples 5, 2, and 4 were found to kill the non-small cell lung cancer cells by inducing apoptosis.

3) Cell Death-Related Protein Assay of Non-Small Cell Lung Cancer Cells

After incubation of the non-small cell lung cancer cells A549 and H460 treated with 50 μM of the compound PB01 or PB11 of Examples 5 and 3 for about 48 hours, the resulting cell culture was added to a lysis buffer (1% Triton X-100, 1 mM EGTA, 1 mM EDTA, 10 mM Tris-HCl, pH 7.4) to lyse cells. The resulting product was put on ice for about 30 minutes, followed by centrifugation to extract proteins and sodium dodecyl sulfate polyacrylamide gel electrophoresis (SDS-PAGE) with 10%-15% gels. After the separated proteins were electrically transferred from the SDS-PAGE gels to nitrocellulose membranes at about 10V for about 2 hours, the nitrocellulose membranes with the proteins were reacted in a blocking buffer (1×TBS, 0.1% Tween-20, 5% skim milk) at room temperature for about 1 hour, treated with primary antibodies, and reacted at about 4° C. overnight. After further reaction with horseradish peroxidase (HRP)-conjugated antigoat, anti-rabbit, and anti-mouse secondary antibodies for about 1 hour, the color was developed using an enhanced chemiluminescence (ECL)-plus system (available from Amersham Biosciences), followed by exposure to an X-ray film. The resulting western blot images are shown in FIG. 10.

Figure 10:
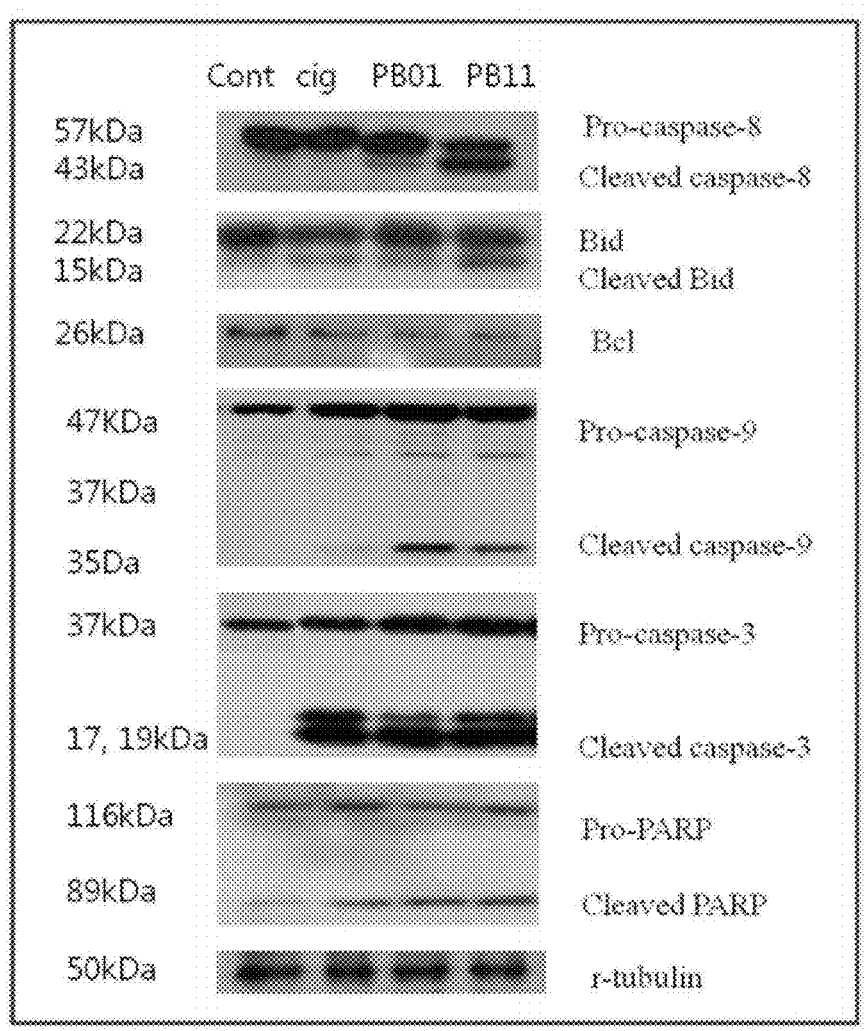
FIG. 10 illustrates images obtained from western blotting following sodium dodecyl sulfate polyacrylamide gel electrophoresis (SDS-PAGE) on proteins extracted from the non-small cell lung cancer cell strain H460 incubated with 50 μM of the compounds PB01 or PB11 of Examples 5 and 3 for about 48 hours.

FIG. 10 illustrates images obtained from western blotting following SDS-PAGE on the proteins extracted from the non-small cell lung cancer cell strain H460 incubated with 50 μM of the compound PB01 or PB11 of Examples 5 and 3 for about 48 hours.

Based on the fact that cell death occurs through apoptosis, found through the above-described experiments, Western blotting as described above was conducted to accurately identify changes in typical intracellular apoptosis-related proteins during a cell death process, and an apoptosis mechanism. As a result, referring to FIG. 10, activity of caspase-8 as an apoptosis-initiating protein was detected. The activities of Bid, caspase-9, caspase-3, and PARP proteins involved in the following stages of apoptosis were also detected. The results indicate that apoptosis is induced through the activation mechanism of these proteins.

Example 10

Radiation Sensitivity Measurement

Figure 11:
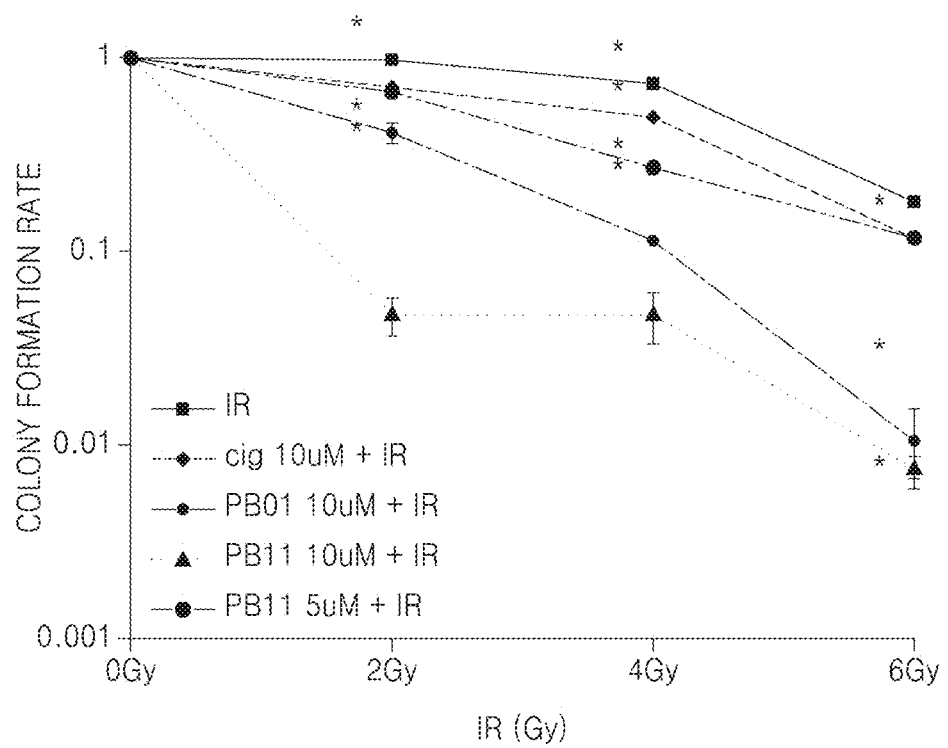
FIG. 11 is a graph illustrating the results of calculating colony formation ratio in the non-small cell lung cancer cell strain H460 on a plate after treatment with ciglitazone (10 μM), PB01 (10 μM), or PB11 (5 μM, 10 μM), irradiation with γ-rays, and then incubation for 14 days.

About 500 cells of non-small cell lung cancer cell strain H460 were floated on each of 60-mm cell culture plates, and then incubated for about 24 hours. After the cells were stably fixed on the bottom of the cell culture plate, the cells were treated with ciglitazone (10 μM), PB01 (10 μM), or PB11 (5 μM, 10 μM), cultured for about 24 hours, and then irradiated with γ-radiation (3.2 Gy/min, Gammacell 3000; Atomic Energy of Canada, Ltd., Mississauga, ON, Canada) at doses of 2 Gy, 4 Gy, and 6 Gy. After incubation for 14 days, followed staining using a 1% crystal violet staining reagent solution (in methanol) to selectively count colonies having a diameter of about 0.5 mm or larger. The colony formation rate of the cells was calculated using the following equation, and the results are shown in FIG. 11.

SF (surviving fraction)=number of colonies formed/
number of cells seeded×plating efficiency of the
control group FIG. 12 illustrates data obtained based on the results of colony counting, representing an effect of the compound PB01 or PB11 of Examples 5 and 3 as a radiation sensitizer when treated in combination with radiation. A dose increase rate of 1 or larger to 2 or less indicates an effect as a radiation sensitizer. Therefore, the compounds of PB01 (10 μM) and PB11 (5 μM) used in combination with radiation at a dose of 4 Gy were found to have a significant effect as radiation sensitizers.

Figure 13:
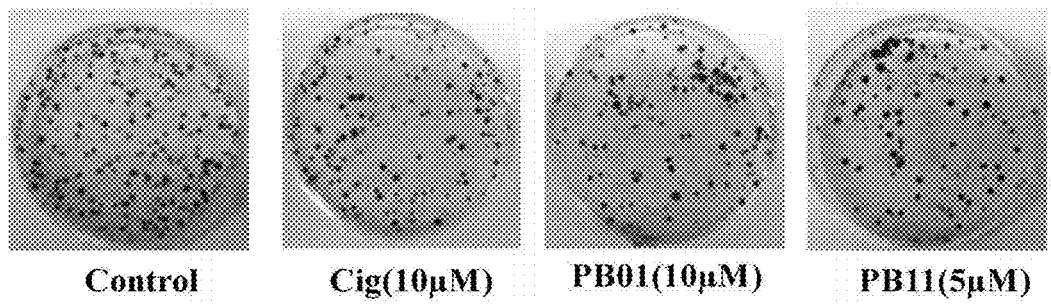
FIG. 13 illustrates visually observed images of colony formation in the non-small cell lung cancer cell strain H460 on a plate after treatment with ciglitazone (10 μM), PB01 (10 μM), or PB11 (5 μM; 10 μM), irradiation with γ-rays, and then incubation for 14 days.

FIG. 13 illustrates visually observed images of colony formation.

As described above, according to the one or more of the above embodiments of the present invention, a novel compound represented by Formula I may function as a PPAR-γ ligand, may have anticancer activity in various types of cancer cells, and may function as an anticancer drug with minimum side effects due to having selective cytotoxicity only to cancer cells. The novel compound may also function as a radiation sensitizer in cancer treatment with radiotherapy.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A method of treating lung cancer breast cancer, colorectal cancer, or leukemia, the method comprising administering a compound of Formula I, a pharmaceutically acceptable salt thereof, or a solvate thereof to a subject in need of such treatment of cancer:

[Formula I]

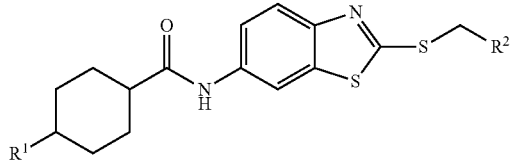

wherein, in Formula I,
—$R^1$ is a $C_1$-$C_3$alkoxy, =O or —OH, and
—$R^2$ is 2H-1,2-oxazine-5-yl, 6H-1,2-oxazine-5-yl, 2H-1,3-oxazine-5-yl, 4H-1,3-oxazine-5-yl, isoxazole-4-yl, or oxazole-4-yl, which is optionally substituted with a $C_1$-$C_3$ alkyl, a $C_1$-$C_3$alkoxy, or hydroxy, wherein the compound of Formula I excludes N-[2-[[(3,5-dimethyl-4-isoxazolyl)methyl]thio]-6-benzothiazolyl]-4-methoxy-cyclohexanecarboxamide.

2. The method of claim 1, wherein —R1 is methoxy.

3. The method of claim 1, wherein the the compound of Formula 1 is selected from the group consisting of 4-oxo-cyclohexanecarboxylic acid [2-(3,5-dimethyl-isooxazole-4-yl-methyl)sulfanyl-benzothiazole-6-yl]-amide; and 4-hydroxy-cyclohexanecarboxylic acid [2-(3,5-dimethyl-isoxazole-4-yl-methyl)sulfanyl-benzothiazole-6-yl]-amide.

4. The method of claim 1, wherein the lung cancer is non-small cell lung cancer.

5. The method of claim 1, wherein the compound of Formula 1, the pharmaceutically acceptable salt thereof, or the solvate thereof functions as a radiation sensitizer for cancer treatment.

\* \* \* \* \*